(12) United States Patent
Weinberger et al.

(10) Patent No.: US 8,450,118 B2
(45) Date of Patent: May 28, 2013

(54) METHOD FOR DETECTING BINDING INTERACTIONS BETWEEN MEMBRANE PROTEINS AND ANALYTES IN A HOMOGENOUS ASSAY

(75) Inventors: Scot Weinberger, Montara, CA (US);
Stephen Dotson, Montara, CA (US);
Nathan Harris, Morgan Hill, CA (US)

(73) Assignee: Molecular Sensing, Inc., Montara, CA (US)

( * ) Notice: Subject to any disclaimer, the term of this patent is extended or adjusted under 35 U.S.C. 154(b) by 220 days.

(21) Appl. No.: 12/799,689

(22) Filed: Apr. 28, 2010

(65) Prior Publication Data
US 2010/0291700 A1  Nov. 18, 2010

Related U.S. Application Data

(60) Provisional application No. 61/215,414, filed on May 4, 2009.

(51) Int. Cl.
*G01N 33/00* (2006.01)
*G01N 21/75* (2006.01)

(52) U.S. Cl.
USPC ............. 436/86; 436/164; 436/165; 436/166; 436/63; 435/7.1

(58) Field of Classification Search
None
See application file for complete search history.

(56) References Cited

U.S. PATENT DOCUMENTS

| | | | |
|---|---|---|---|
| 5,325,170 A | 6/1994 | Bornhop et al. | |
| 5,922,594 A | 7/1999 | Lof.ang.s | |
| 6,381,025 B1 | 4/2002 | Bornhop et al. | |
| 6,381,925 B2 | 5/2002 | Rejcek et al. | |
| 6,809,828 B2 | 10/2004 | Bornhop et al. | |
| 7,045,171 B2 | 5/2006 | Bookbinder et al. | |

(Continued)

FOREIGN PATENT DOCUMENTS

| | | |
|---|---|---|
| WO | WO 2004/023115 A1 | 3/2004 |
| WO | WO 2006/047408 A2 | 5/2006 |
| WO | WO 2009/039466 A1 | 3/2009 |

OTHER PUBLICATIONS

Persson et al. "Lipid-Based Passivation in Nanofluidics", Nano Lett. 2012, 12, pp. 2260-2265.*
Suzuki et al. "Planar lipid bilayer or reconstitution with a microfluidic system", Lab Chip, 2004, pp. 502-505.*
Bornhop et al. (2007) "Free-Solution, Label-Free Molecular Interactions Studied by Back-Scattering Interferometry." *Science*, 317(1732): 1732-1736.

(Continued)

*Primary Examiner* — Yelena G Gakh
(74) *Attorney, Agent, or Firm* — Quine Intellectual Property Law Group, P.C.; John Storella

(57) ABSTRACT

Devices and methods for detecting interaction between components associated with lipid membranes and analytes are described herein. In certain methods, a surface of a compartment of a device is coated with a material that attaches to lipid membrane from a sample. An analyte is introduced and interaction is detected, for example, by back scattering interferometry. In another method, a surface is passivated with a material that does not bind a lipid membrane. A sample is introduced that contains a membrane comprising a component for testing and an analyte. Interaction is detected. In a third method, a channel is filled with a first liquid that does not comprise a lipid membrane. A bolus of a second liquid that comprises a membrane comprising a component for testing and an analyte is introduced under laminar flow conditions so that a leading edge of the second liquid does not completely displace the first liquid in a sensing area that is interrogated by optical methods, for example, a laser. Interaction between the analyte and the component is detected.

17 Claims, 14 Drawing Sheets

U.S. PATENT DOCUMENTS

| | | |
|---|---|---|
| 7,130,060 B2 | 10/2006 | Bornhop et al. |
| 7,835,013 B2 | 11/2010 | Jones et al. |
| 2002/0002353 A1 | 1/2002 | Michal et al. |
| 2002/0034580 A1 | 3/2002 | Yang et al. |
| 2003/0087099 A1 | 5/2003 | Merrill et al. |
| 2004/0241765 A1 | 12/2004 | Zweig |
| 2006/0012800 A1 | 1/2006 | Bornhop et al. |
| 2006/0268260 A1 | 11/2006 | Liu et al. |
| 2006/0275825 A1* | 12/2006 | Baird et al. .................... 435/7.1 |
| 2009/0103091 A1 | 4/2009 | Jones et al. |
| 2009/0185190 A1 | 7/2009 | Weinburger et al. |
| 2009/0325199 A1 | 12/2009 | Geddes |
| 2010/0188665 A1 | 7/2010 | Dotson et al. |

OTHER PUBLICATIONS

Gavutis et al. (2005) "Lateral ligand-receptor interaction on membranes probed by simultaneous fluorescence-interference detection." *Biophysics Journal*, 88(6): 4289-4302.

Molphy et al. (1994) "Surface modification of kaolin. !. Covalent attachment of polyethylene glycol using a urethane linker." *Polymer International*, 34: 425-431.

Zhang et al. (1998) "Protein and cells on PEG immobilized silicon surfaces." *Biomaterials*, 19: 953-960.

\* cited by examiner

*0.195 nM concentration removed as saturation appears to occur at 0.097 nM

METHOD FOR DETECTING BINDING INTERACTIONS BETWEEN MEMBRANE PROTEINS AND ANALYTES IN A HOMOGENOUS ASSAY

CROSS-REFERENCE TO RELATED APPLICATIONS

This application claims the benefit of the priority date of U.S. application 61/215,414, filed May 4, 2009.

STATEMENT AS TO FEDERALLY SPONSORED RESEARCH

None.

BACKGROUND OF THE INVENTION

Membranes are the outer container of a cell which is comprised mainly of proteins and lipids. As such, the membrane of the cell has a vital role in the process of all living things. The membrane has processes for transporting molecules into and out of the cell. This transport process has important roles, and can be either active or passive. The active process requires energy to take place. The passive process includes diffusion, osmosis, and filtration. These transport processes regulate cell volume, maintain intracellular pH and ionic composition in a narrow range, extract and concentrate metabolic fuels and building blocks and exude toxic substances. They also generate ionic gradients for excitability of nerve and muscle.

As membranes play such a vital role in the processes of life, understanding and monitoring the different interactions with membranes provides information that can lead to improved health care. In the study of membranes or membrane fractions, it is important to remember that the internal and external component of the membrane are different.

Biological membranes have many components that are involved in regulating entry of molecules into or out of a cell, or in transmitting signals from messengers, such as hormones, into a cell. Such components can comprise proteins, such as G protein-coupled receptors, ion-channel receptors, tyrosine kinase-linked receptors and cytokine receptors. Identifying molecules that block or interfere with the interaction between these components and their natural binding partners is an important area of pharmaceutical research. The use of isolated membrane components for studies allows for concentration of the molecules, but also removes them from their natural environment. One challenge in using membrane bound components for such tests is the small amount of the component in a membrane: In order to be able to detect an interaction between a membrane component and a binding partner, both molecules must be in concentration above the sensitivity threshold of the instrument used for detection.

In certain methods, membrane material can be bound to a solid support. Such devices are described, for example, in U.S. Pat. No. 5,922,594 (Lot) and U.S. Pat. No. 7,045,171 (Bookbinder).

Back-scattering interferometry ("BSI") is a method useful for detecting interactions between molecules in a sample. A version of the method was described in U.S. Pat. No. 5,325,170 (Bornhop et al., Jun. 28, 1994). The method described there involves directing a laser beam onto a channel to produce back-scattered light in the form of an interference fringe pattern. The form and location of the fringe pattern is a function of the refractive index of the liquid being interrogated. Binding events between molecules in the fluid, such as target-receptor interactions, change the refractive index of the fluid and result in a shift in the location of the fringe pattern. Detecting shifts in the fringe pattern is a way of detecting binding events in the fluid.

BSI allows for both homogenous assays, in which both binding partners are in free solution, and heterogenous assays in which one of the binding partners is tethered to the surface of the channel. U.S. Pat. No. 6,381,025 (Bornhop et al., Apr. 30, 2002) describes a method for performing back-scattering interferometry in which a channel having a generally hemispherical cross-sectional shape is disposed in a micro-fabricated substrate. U.S. Pat. No. 6,809,828 (Bornhop et al., Oct. 26, 2004) describes a chip for back-scattering interferometry in which the substrate has a channel taking the form of a rectangle. U.S. Pat. No. 7,130,060 (Bornhop et al., Oct. 31, 2005) describes a method for determining absolute refractive index using back-scattering interferometry in which light is directed at a capillary tube and refractive index is determined as a function of the angle at which there is a marked change in intensity. Bornhop et al., Science, 317:1732, Sep. 21, 2007, describes free-solution, label-free molecular interactions investigated by back-scattering interferometry.

SUMMARY OF THE INVENTION

In one aspect this invention provides a method comprising detecting interaction between a component disposed in a lipid membrane and an analyte in a test sample, wherein the concentration of the component in the test sample is less than 1 micromolar. In one embodiment the concentration of the component is less than 1 nanomolar. In another embodiment the concentration of the component is less than 100 picomolar. In another embodiment the component comprises a protein. In another embodiment the method is label-free.

In one aspect this invention provides a method comprising detecting interaction between a component disposed in a lipid membrane and an analyte in a test sample, wherein the concentration of the component in the test sample is less than 1 micromolar. In one embodiment the concentration of the component is less than 1 nanomolar. In another embodiment the concentration of the component is less than 100 picomolar. In another embodiment the component comprises a protein. In another embodiment the method is label-free.

In another aspect this invention provides a method comprising using back-scattering interferometry to detect interaction between a component disposed in a lipid membrane and an analyte in a sample. In one embodiment the membrane and the analyte are in free solution.

In another aspect this invention provides an instrument comprising: a coherent light source; a fluidic device comprising a fluidic channel comprising a sensing area interrogated by coherent light from the coherent light source, wherein the sensing area comprises a first fluid that does not comprise a lipid bilayer and a second fluid comprising a lipid bilayer, wherein the first fluid surrounds the second fluid in the sensing area; and a detector to detect the back-scattered light. In another embodiment, the fluidic device is a microfluidic device and comprises a microfluidic channel.

In another aspect this invention provides a method comprising: providing a fluidic device comprising a channel, wherein the channel comprises a sensing area for interrogation by an optical detector; moving a first liquid through the sensing area; moving a bolus of a second liquid through the sensing area under laminar flow conditions so that during a detection period the second liquid does not completely displace the first liquid in the sensing area, wherein the second liquid comprises a lipid membrane comprising a component and an analyte that binds the component; and interrogating the sensing area during the detection period with an optical detector to detect signal. In one embodiment the device is a microfluidic device or microchip or a capillary tube. In another embodiment the device comprises glass, quartz, borosilicate, silica (e.g., fused silica) or a polymeric material (e.g., a plastic such as polyacrylate, cyclic olefin copolymer, polydimethyl siloxane, polycarbonate, and polymethyl methacrylate). In another embodiment the channel has a cross sectional area in the sensing area of less than 1 mm². In another embodiment the channel has a cross sectional area in the sensing area of about 0.2 mm². In another embodiment In another embodiment the sensing area has a volume between about 350 pl and about 1000 nl. In another embodiment the sensing area has a volume between about 0.1 nl and about 10 nl. In another embodiment the channel is a capillary tube and the sensing area has a volume between about 10 nl and about 100 nl. In another embodiment the first liquid comprises an aqueous buffer and a detergent. For example, the buffer can be selected from PBS, PIPES, MOPS, TES, HEPES, Trizma, Tricine and CAPSO. The detergent can be selected from Triton, Tween and octyl-beta-D-galactopyranoside. In another embodiment the method comprises moving the bolus through the sensing area at a rate between about 0.2 mm/sec to about 3.3 mm/sec. In another embodiment the lipid membrane comprises a G protein-coupled receptor, an ion-channel receptor, a tyrosine kinase-linked receptor, a cytokine receptor or an enzyme. In another embodiment the lipid membrane comprises a cell membrane. In another embodiment the lipid membrane comprises a lipid bilayer. In another embodiment the lipid membrane comprises a vesicle or a liposome. In another embodiment the sensing area is configured to generate back-scattered light when interrogated by a coherent light beam and the optical detector uses back-scattering interferometry. In another embodiment the method comprises converting the detected signal into a parameter related to refractive index of the liquid in the sensing area. In another embodiment the method comprises determining an amount of binding between the analyte and the lipid membrane. In one embodiment determining comprises comparing the detected signal with signal detected from a control sample.

In another aspect this invention provides an instrument comprising: (i) a coherent light source; (ii) a fluidic device comprising a fluidic channel comprising a surface to which a lipid membrane is attached, wherein the channel is configured to produce back-scattered light when interrogated by coherent light from the coherent light source; and (iii) a detector to detect the back-scattered light. In another embodiment the coherent light source is a laser. In another embodiment the fluidic device is a microfluidic device or microchip. In another embodiment the channel in the detection zone has a cross sectional area of less than 1.0 mm² In another embodiment the channel has an average cross sectional area of about 0.2 mm². In another embodiment the channel has an average cross sectional area of about 0.003 mm². In another embodiment the fluidic device comprises a second channel. In another embodiment the lipid membrane is attached to the surface through a non-covalent bond with a membrane binding moiety. In another embodiment the detector comprises a bi-cell position sensor, a linear or area array CCD or CMOS camera and laser beam analyzer assembly, a slit-photodetector assembly, and/or an avalanche photodiode. In another embodiment the instrument further comprises a computer programmed to convert the detected back-scattered light into a parameter related to refractive index. In another embodiment the surface comprises glass, quartz, borosilicate, silica (e.g., fused silica) or a polymeric material (e.g., a plastic such as polyacrylate, cyclic olefin copolymer, polydimethyl siloxane, polycarbonate, and polymethyl methacrylate). In another embodiment the bifunctional linker comprises a silane moiety. In another embodiment the reactive group is a thioesther and the second reactive group is an amine. In another embodiment the surface comprises free hydroxyl groups and method comprises: (i) reacting a mercapto-alkyloxysilane with the hydroxyl groups to bind the silane to the surface; (ii) reacting the mercapto group with a maleimide succinic esther to generate a thioesther moiety; and reacting the thioesther moiety with a molecule comprising an amine and a membrane binding moiety to generate a thiocarbamate bond. In another embodiment the molecule does not comprise a hydrophilic domain. In another embodiment the membrane is attached to the surface through a non-covalent bond with a membrane binding moiety attached to the surface. In another embodiment the membrane binding moiety is selected from a hydrophobic or amphiphilic moiety with straight or branched chain alkyl, alkynyl, alkenyl, aryl, araalkyl, heteroalkyl, heteroalkynyl, heteroalkenyl, heteroaryl, or heteroaraalkyl. In another embodiment the membrane binding moiety comprises a $C_{10}$ to $C_{25}$ straight or branched chain alkyl or heteroalkyl. In another embodiment the membrane binding moiety comprises a $C_{10}$ to $C_{25}$ straight chain alkyl. In another embodiment the membrane binding moiety comprises a $C_{16}$ straight chain alkyl. In another embodiment the membrane binding moiety is covalently attached to the surface. In another embodiment the membrane binding moiety is covalently attached to the surface through a bifunctional linker. In one embodiment the bifunctional linker comprises a silane attached to the surface and a thiocarbamate attached to the membrane binding moiety. In another embodiment the lipid membrane is attached only to a portion of the channel surface. In another embodiment the lipid membrane comprises a cell membrane, lipid bilayer, a vesicle or a liposome.

In another aspect this invention provides a method comprising: (a) providing an instrument comprising: (i) a coherent light source; (ii) a fluidic device comprising a fluidic channel comprising a surface to which a lipid (iii) membrane is attached, wherein the channel is configured to produce back-scattered light when (iv) interrogated by coherent light from the coherent light source; and (v) a detector to detect back-scattered light; (b) introducing sample comprising an analyte into the channel; and (c) detecting binding between the analyte and the lipid membrane. In one embodiment, the fluidic device is a microfluidic device or a microchip. In another embodiment the lipid membrane comprises a cell membrane, lipid bilayer, a vesicle or a liposome. In another embodiment the analyte is selected from a small organic molecule, a biopolymer, a macromolecular complex, a virus or a cell. In one embodiment detecting binding comprises detecting back-scattered light from the channel, converting the detected back-scattered light into a measure of refractive index and correlating the measure with a measure indicating binding.

In another aspect this invention provides an instrument comprising: (a) a coherent light source; (b) a fluidic device comprising a fluidic channel comprising a surface to which a layer of passivating material is attached, wherein the passivating material is configured not to bind lipid membrane introduced into the channel, wherein the channel is configured to produce back-scattered light when interrogated by coherent light from the coherent light source; and (c) a detector to detect the back-scattered light. In one embodiment the channel further comprises a sample comprising a lipid membrane comprising a component and an analyte that binds the component and the passivating material comprises a lipid membrane that does not comprise the component.

In another aspect this invention provides a method comprising: (a) providing an instrument comprising: (i) a coherent light source; (ii) a fluidic device comprising a fluidic channel comprising a surface to which a layer of passivating material is attached, wherein the passivating material is configured not to bind lipid membrane introduced into the channel, wherein the channel is configured to produce back-scattered light when interrogated by coherent light from the coherent light source; and (iii) a detector to detect the back-scattered light; (b) introducing into the channel a sample comprising a lipid membrane comprising a component and an analyte that binds the component; and (c) detecting binding between the analyte and the lipid membrane. In one embodiment, the passivating material comprises a lipid membrane that does not comprise the component.

The fluidic channel is interrogated by a light source and can take any shape appropriate to produce back-scattered light.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

1. Introduction

Figure 1:
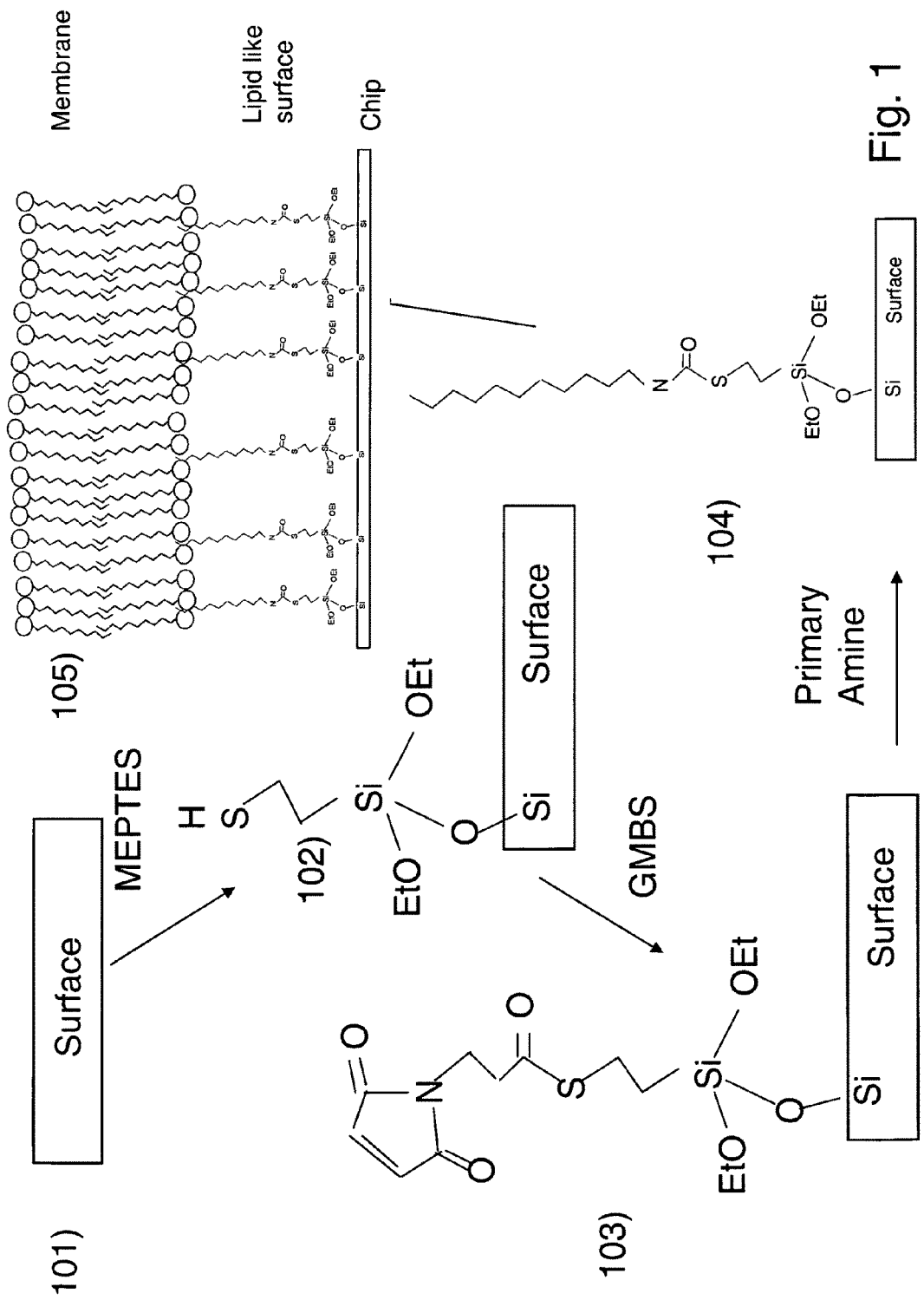
FIG. 1 is a schematic representation of a manufacturing process to attach a membrane to a surface. A surface with active groups (e.g., hydroxyl groups) (101) can be reacted with a thioalkyl silane to coat the surface with available thiol groups (102). This can further be reacted to place an active thioesther group on the surface (103). The thioesther group can be reacted with an amino alkane or other lipid-like moiety to produce a lipid-like surface (104). This surface will bind membrane through hydrophobic interactions.

This invention is directed to devices and methods for detecting interactions between components embedded in a lipid membrane and other molecules to which they are exposed. Certain of these methods are label-free. Certain methods are homogenous, that is, the analytes are in free solution. Other methods involve non-homogenous assays, that is, one member of the binding pair is tethered, covalently or non-covalently, to a solid support, such as the wall of a container in which the measurement takes place. In certain embodiments, the concentration of the membrane components in the volume of solution being interrogated is very low, for example, no more than 1 micromolar, no more than 1 nanomolar or no more than 100 picomolar. The sensitivity of these methods can be achieved using back-scattering interferometry.

This invention provides methods of detecting interaction between an analyte and a membrane or lipid layer comprising lipid and a component that interacts with the analyte. The ability to detect binding between binding partners is a function of several variables. One of these is the sensitivity of the instrument being used. Another is the concentration of the least concentrated member of the binding pair. In binding assays for membrane components, such as proteins, the nascent concentration of the target can be low. Solutions to these problems include using protein isolated from a membrane and using membranes in which the component is artificially over-expressed. However, both of these methods involve environments that are different than the environment of the component in a native membrane. Another factor is the relative size of the analyte compared with the target. The larger the discrepancy, the more difficult to detect binding signal over noise in the system, for label-free approaches. In the case of components associated with membranes, the entire complex of lipid and associated components can be quite large compared with the analyte, making label-free detection highly problematic.

2. Back-Scattering Interferometry

A back-scattering interferometer typically comprises an optical assembly and electronics to analyze an optical signal. The optical assembly can be mounted on an optical bench. Back-scattering interferometers are well known in the art. They are described, for example, in U.S. Pat. Nos. 5,325,170; 6,381,925; 6,381,025; 6,809,828 and 7,130,060; International applications WO 2004/023115, WO 2006/047408 and WO 2009/039466; and U.S. patent publications U.S. 2006-0012800 and U.S. 2009-0185190.

The optical assembly comprises the following elements: First, a fluidic container having a compartment for holding a sample. A portion of the container in which the sample is contained functions as an interrogated volume, sensing area or detection zone. Second, the optical assembly comprises a coherent light source positioned to direct a beam toward the sensing area, wherein the path of the beam defines an optical train and generates a back-scattered light pattern, also called an interference fringe pattern. Third, the optical assembly comprises a photo-detector configured to detect the back-scattering light pattern. Typically, the instrument also will comprise a computer that converts the fringe pattern into a measure or indicator of refractive index. Optionally, the instrument comprises a temperature regulator that can maintain a stable temperature at least within the fluid during periods of measurement.

Several factors influence the generation of an interference pattern: Reflection, refraction and retardation (of the light beam). The coherent light beam should be large enough so that it passes across a non-flat surface from the container into the liquid. Accordingly, the compartment should comprise a curve or an edge (e.g., a corner) through which the light passes in order to generate a useful interference pattern.

2.1 The Container

The container used in this invention is adapted for use in back-scattering interferometry. The container is adapted to generate a back-scatter fringe pattern when filled with liquid and interrogated with a focused or unfocused coherent light source, such as a laser beam. Factors that influence the ability to create such a pattern include the relative refractive indices of the substrate that forms the container and the liquid within, as well as the shape of the compartment in which the liquid is contained and the light source strikes.

The container can take the shape of a chip (e.g., a microchip). As in known in the art, chips can accommodate a plurality of channels or other features due to having one very thin dimension compared with their other dimensions. Including a plurality of channels allows one to perform matched experiments, to use one channel as a control against which to compare a test sample, and to perform multiple experiments in one chip. The container also can take the shape of a tube, such as a microcapillary tube. See, e.g., U.S. patent application Ser. No. 12/655,899, filed Jan. 8, 2010.

2.1.1 Container Material

The container should be made of a material that has a different (e.g., higher) refractive index than the sample inside. The container can be formed of any suitable optically transmissive material, such as glass, quartz, borosilicate, silica (e.g., fused silica) or a polymeric material, e.g., a plastic such polystyrene, polysulfone, polyetherimide, polyethersulfone, polysiloxane, polyester, polycarbonate, polyether, polyacrylate, polymethacrylate, cellulose, nitrocellulose, a perfluorinated polymer, polyurethane, polyethylene, polyamide, polyolefin, polypropylene or nylon.

2.1.2 Compartment Shape and Size

The container will have an internal compartment that can hold the sample. Typically, the compartment will take the shape of a bore. The bore may have a curved cross section that is, for example, circular, hemi-circular, rectangular, elliptical or substantially any of these. Back-scatter fringe patterns are easily produced when the substrate includes a compartment having curved or angular walls through which the light passes to reach the sample. In certain embodiments, the compartment takes a long, thin shape, such as a channel, column, cylinder or tube.

The container also is adapted to receive a liquid sample. In certain embodiments, the container is adapted to function as the collection unit of the sample from its primary source, e.g., a subject organism. For example, the container can comprise a channel or tube that opens at two ends of the container. For example, the container can be a capillary tube or a hematocrit tube, or a chip comprising a channel that opens at different sides of the chip.

The container can take the shape of a capillary tube or micro-hemotcrit tube. The tube can be, for example, approximately 75 mm long, with fire-polished ends that can easily be sealed if desired. The tube can be coded with a red band to designate heparin coating. It can contain at least 2 U.S.P. units of cation-free ammonium heparin. It can have an internal diameter of 1.1 mm to 1.2 mm with a wall of 0.2 mm±0.02. The volume of the compartment can be between 100 nanoliters and 10000 microliters (10 milliliters), between 1 microliter and 1 milliliter, between 10 microliters and 1 milliliter or between 50 microliters and 250 microliters. Furthermore the tube can have dimensions as follows: Outside diameter 0.75 mm to 2.0 mm, inside diameter from 0.05 mm to 1.5 mm.

In some embodiments, the channel is a microfluidic channel. Microfluidic channels generally have a cross sectional area of less than 1 mm$^2$. In other embodiments, the channel has cross sectional area of about 0.01 mm$^2$, about 0.02 mm$^2$, about 0.03 mm$^2$, about 0.04 mm$^2$, about 0.05 mm$^2$, 0.06 mm$^2$, about 0.07 mm$^2$, about 0.08 mm$^2$, about 0.09 mm$^2$, about 0.1 mm$^2$, about 0.2 mm$^2$, about 0.3 mm$^2$, about 0.4 mm$^2$, about 0.5 mm$^2$, about 0.6 mm$^2$, about 0.7 mm$^2$, about 0.8 mm$^2$, about 0.9 mm$^2$, or about 1.0 mm$^2$.

In other embodiments the channel has a diameter no greater than any of: about $1.0\times10^4$ µm, about $9\times10^3$ µm, about $8\times10^3$ µm, about $7\times10^3$ µm, about $6\times10^3$ µm, about $5\times10^3$ µm, about $4\times10^3$ µm, about $3\times10^3$ µm, about $2\times10^3$ µm, about $1\times10^3$ µm, about $9\times10^2$ µm, about $8\times10^2$ µm, about $7\times10^2$ µm, about $6\times10^2$ µm, about $5\times10^2$ µm, about $4\times10^2$ µm, about $3\times10^2$ µm, about $2\times10^2$ µm, about $1\times10^2$ µm, about $9\times10$ µm, about $8\times10$ µm, about $7\times10$ µm, about $6\times10$ µm, about $5\times10$ µm, about $4\times10$ µm, about $3\times10$ µm, about $2\times10$ µm, about $1\times1$ µm, about 9 µm, about 8 µm, about 7 µm, about 6 µm, about 5 µm, about 4 µm, about 3 µm, about 2 µm, about 1 µm, about 0.9 µm, about 0.8 µm, about 0.7 µm, about 0.6 µm, about 0.5 µm, about 0.4 µm, about 0.3 µm, about 0.2 µm, or about 0.1 µm. In other embodiments the channel has a diameter no greater than 500 µm, e.g. between 0.1 micron and 500 microns.

In certain embodiments the analyte is detected as a result of its binding to a binding agent. In this case, the binding agent for an analyte in a sample that one is testing for can be immobilized on the wall of the compartment (heterogeneous assay) or allowed to remain free in solution after the sample is added (homogeneous assay). Binding partners include, for example, antibodies and antibody-like molecules, receptors, nucleic acids (e.g., oligonucleotides). In another embodiment, the agent can be an enzyme or enzyme complex (mixture) which catalyzes an enzymatic reaction which can degrade sample components such as cells, cell fragments, and/or biomolecules. In another embodiment the agent could be an enzyme or enzyme complex (mixture) which catalyzes the creation of new biomolecules arising from the fusion of biomolecular species (such as a ligase) or replication—amplification of biomolecular species, as is the case in polymerase chain reactions.

Moreover, the surfaces of the sample container could be coated with a material to minimize unwanted interactions with the walls of the container. Such surfaces would include polymeric coatings, such as dextran, Teflon, polyethylene glycol, etc. Furthermore, the surfaces of the container could be coated with biospecific reagents for selective capture of target analytes or selective enzymatic modification of target analytes as described above.

2.2 Container Mounting/Temperature Regulation

The device of this invention typically comprises a mounting adapted to receive the container and position it for interrogation by the coherent light source. The mounting can be removable from the frame of the device. The mounting can be attached to an optical bench that comprises other components of the optical system. The mounting can comprise a fastener to fasten the container to the mounting. If the container is a tube, the mounting can comprise, for example, a clip or set of clips, a surface with an indentation adapted to receive the tube, in which it can rest, an adhesive material, or a holder in which the container is inserted and held, e.g., a cylinder in which a tube is slid within and retained, a flat mounting stage on which a chip is locked into position. In certain embodiments the mount is in thermal contact with a temperature control assembly such as a Peltier device to insure homogeneous control of temperature as required to perform high sensitivity BSI measurements (+/−1-5 millidegree C.). See, for example, U.S. patent publication 2009-0185190 (Jul. 23, 2009).

A container of the invention can be adapted and configured to fit snugly within a holder. The container can be held in place by a positioner, such as a metal plate with tightening screws. The container can be manually inserted into the holder or cartridge. In an embodiment, the container is disposable while the holder can be used for numerous different chips with a device of the invention. A holder retention mechanism can be used to firmly hold the chip in the holder along the axis of the mechanism. The container and/or the thermal subsystem can be affixed to a translation stage that allows adjustment of the chip relative to the laser beam. For example, the container can be tilted slightly (for example, approximately 7°) so that the back-scattered light from the sensing area of the container can be directed onto the photodetector.

In experiments that involve comparing the interference pattern between two samples (e.g., a test and control sample), the samples can be measured simultaneously or in sequence. In simultaneous measurements the two samples can be loaded onto the interferometer and a beam splitter can split the laser beam and direct it to each of the two samples. Alternatively, the beam can be made wide enough so that a single beam covers both fluid compartments. In one embodiment, the first and second samples are comprised in different containers, e.g., tubes, and one tube is tilted or rotated, e.g., 3° to 7° with respect to the other tube. This results in the interference signal from each container being directed to different parts of the detector so that they are distinguishable.

In another embodiment, the first and second samples are located within a single tube, where the first sample represents a region of the sample container that contains a selectively deposited binding molecule for extraction and subsequent analysis of a target of interest, and where the second or reference sample represents a region of the sample container that is free of binding molecule, or moreover is coated with a specific passivating agent to minimize unwanted non-specific binding of the target of interest.

Sample can be introduced into the container by any method known. For example, the sample can be introduced manually using a syringe, e.g., manual pipetter. Also, sample can be introduced into the container using a fluidics robot, such as any commercially available robot, e.g., from Beckman or Tecan.

2.3 Coherent Light Source

Examples of coherent light sources for use with the invention include, but are not limited to, a laser, for example a He/Ne laser, a VCSEL laser, and a diode laser. The coherent light may be coupled to the site of measurement by known wave-guiding or diffractive optical techniques or may be conventionally directed to the measurement site by free space transmission. The coherent light is preferably a low power (for example, 3-15 mW) laser (for example, a He/Ne laser). As with any interferometric technique for chemical analysis, the devices and methods of the invention benefit from many of the advantages lasers provide, including high spatial coherence, monochromaticity, and high photon flux. The beam can be directed directly to a sensing area on the fluidic chamber or to a mirror that is angled with respect to the plane of propagation of the laser beam, wherein the mirror can redirect the light onto the sensing area. In another embodiment, the coherent light is preferably generated by a solid state laser source such as a light emitting diode or vertical cavity surface emitting laser (VCSEL), for which requisite beam characteristics of monochromaticity and beam coherence is achieved. In an embodiment, the coherent light source generates an easy to align collimated laser beam that is incident on a sensing area of the container for generating the back-scattered light.

A coherent light source can have a cross-sectional area of at least 0.2 mm$^2$. The cross-section can take the shape of a circle, an elipse or other oblong configurations.

2.4 Detector

A photodetector can be configured and incorporated into a device of the invention to detect a fringe pattern produced by back-scattered light from a sensing area on a container. The pattern is based on the contents and/or composition of the sample. In an embodiment, qualitative and quantitative measurements are performed by forming molecular complexes, such as antibody-antigen or drug target-drug candidate. In an embodiment, the photodetector detects a qualitative or quantitative value of an analyte in a liquid sample, for example, the amount of a specific antigen in a blood sample or host antibody titer towards a given antigen.

The photodetector can be one of any number of image sensing devices, including a bi-cell position sensor, a linear or area array CCD or CMOS camera and laser beam analyzer assembly, a slit-photodetector assembly, an avalanche photodiode, or any other suitable photodetection device. The back-scattered light comprises interference fringe patterns that result from the reflective, refractive, and retardation interaction of the incident laser beam with the walls of the sensing area and the sample. These fringe patterns include a plurality of light bands whose positions shift as the refractive index of the sample is varied, for example, through compositional changes. For example, a sample in which two components bind to each other can have a different refractive index than a sample in which the two components do not bind. In an embodiment, the photodetector detects the back-scattered light and converts it into one or more intensity signals that vary as the positions of the light bands in the fringe patterns shift. For fringe profiling, the photodetector can be mounted above the chip at an approximately 45° angle thereto. Fringe profiling can also be accomplished by detecting the direct back-scatter. In an embodiment, the fringes can be profiled in direct back-scatter configuration and direct them onto the camera which is at 90° from the beam, in this way, the packaged device can remain small while maximizing the resolution for measuring a positional shift, for example, the effect of angular displacement.

The optical detector can be placed at a distance that optimizes the number of interference fringes detected and resolution. For example, typically, the detector should receive signal from at least one-fringe-width to detect movement of the fringe. However, receiving signal from at least two fringe-widths can be useful. Resolution can be a function of density of pixels in the CMOS or CCD camera. So, for example, using a CCD detector with a pixel density of 1316 pixels per inch, the detector can usefully be placed about 100 mm to 600 mm from the chip surface, e.g., about 270 mm.

2.5 Detection

The photodetector can detect the back-scattered light fringe pattern and, in combination with computer algorithms, convert it into signals that can be used to determine a parameter of refractive index (RI), or an RI related characteristic property, of the sample. For example, the RI of a sample with a certain concentration of analyte in the sample can be slightly different than the RI of a sample where the analyte is present in the sample in a different concentration. A signal analyzer, such as a computer or an electrical circuit, can be employed to analyze the photodetector signals and determine the characteristic property of the sample. Positional shifts in the light bands relative to a baseline or a reference value can then be detected by a photodetector and computed using a processor, such as a PC. The device can provide a signal (for example, positional shifts in the light bands) that is proportional to abundance of the analyte. Preferably, the signal analyzer includes the programming or circuitry necessary to determine from the positional shift of the formed fringes, the RI or other characteristic properties of the sample to be determined, such as temperature or flow rate, for example. The parameter of refractive index can be, for example, the position of the bands on some scale of location. This position can be displayed as a number or as coordinate on a graph. For example, the coordinate on the Y axis can change over time on the X axis. The parameter can be quantitatively related to sample refractive index.

The signal analyzer can be a computer which, optionally, controls other aspects of the system. The computer functions to perform the calculations necessary to detect the fringe movement and output the data on the user interface. Moreover, the computer can function to store and retrieve method files which automate the performance of an assay or analysis, provides data analysis tools to determine binding profiles, qualitative measurements, and quantitative measurements, as well as providing a means to calibrate the system for total gain and output based upon a reference sample.

The photodetector can be a camera, such as a CCD camera. The camera captures the image of the fringe pattern. A CCD camera can typically collect from one to sixty images per second. The image can be projected on a monitor for visual analysis. For example, the monitor can be calibrated and/or the operator can visually detect changes in the fringe pattern over time. Alternatively, the image can be subjected to a variety of mathematical algorithms to analyze the fringe pattern. Examples of algorithms used to analyze fringe pattern are Fourier transforms, Gaussian fit with or without hamming window and sinusoidal correction.

Figure 3:
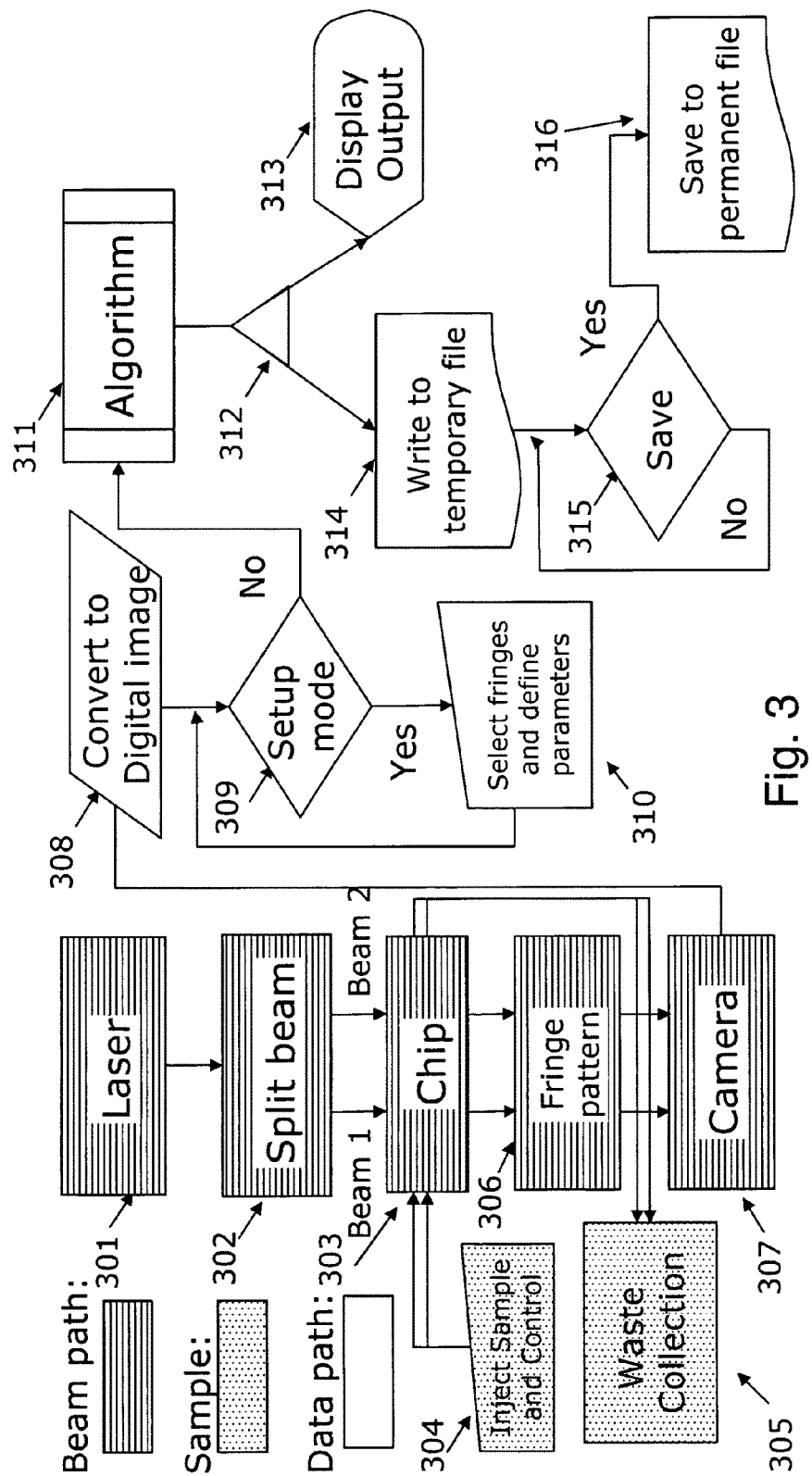
FIG. 3 shows a flow diagram for back-scattering interferometry.

FIG. 3 depicts a flow diagram of a BSI system. A laser 301 produces a beam that passes through a beam splitter 302 to create two beams. A beam splitter is optional but useful for comparing first and second samples. These two beams impinge onto a chip 303. The two-channel chip allows for the injection of samples and controls 304. The liquid that is injected passes through the chip 303 and then is collected as waste 305. The interaction of the beams and the channels creates fringe patterns 306. These two fringe patterns 306 are directed onto a camera 307. The data acquired from the camera 307 is converted into a digital image 308. Initially, the program is started in setup mode 309, which allows the user to select the fringes to be analyzed and define the parameters of the analysis 310. Once setup mode 309 is turned off, the digital image 308 is passed to an algorithm 311 that calculates shifts in the fringe pattern 306. This output is split 312 to a real time output display 313 and is also written to a temporary file 314. At any time the user can save the data 315, which then writes the data to a permanent file 316.

Figure 4:
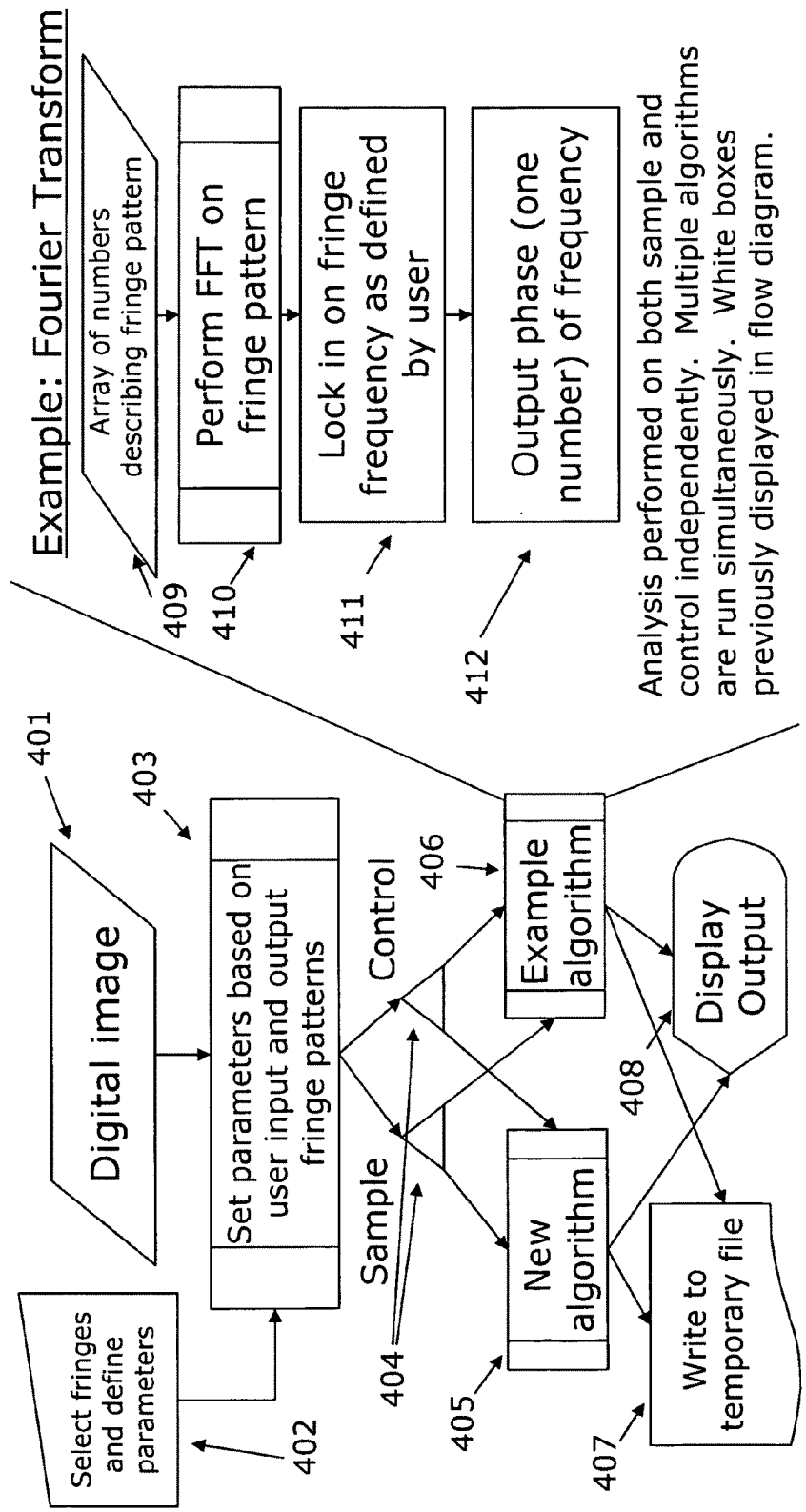
FIG. 4 shows a Fourier transform algorithm that transforms a digital image into a function that describes the image.

FIG. 4 shows a diagram of the digital image process 401 with the Fourier transform algorithm as an example. The Fourier transform transforms a digital image into a function that describes the image 409 and 410. Phase changes for the predominant spatial frequency 411 in the Fourier transform over time can indicate shifts in the fringe pattern 412.

Figure 5:
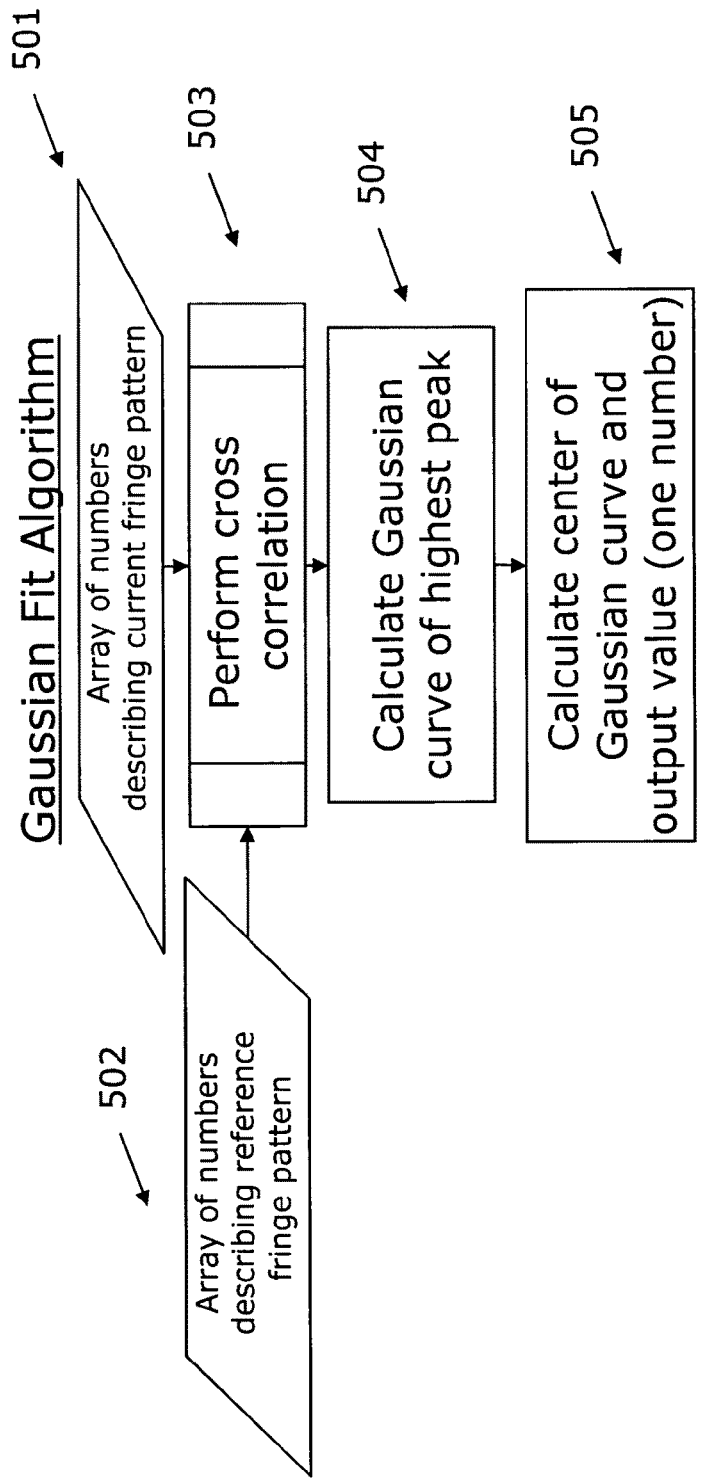
FIG. 5 shows a flow chart for the Gaussian fit analysis.

FIG. 5 shows the Gaussian fit analysis. A cross-correlation 503 is performed on a reference fringe pattern 502 and a new pattern 501. A Gaussian fit is calculated 504 from the highest peak of the cross-correlation. The calculated center of the Gaussian fit 505 is used to measure the pixel shift, which allows for sub-pixel shift detection. This method is described in more detail in U.S. Ser. No. 12/665,898, filed Jan. 8, 2010.

Figure 6:
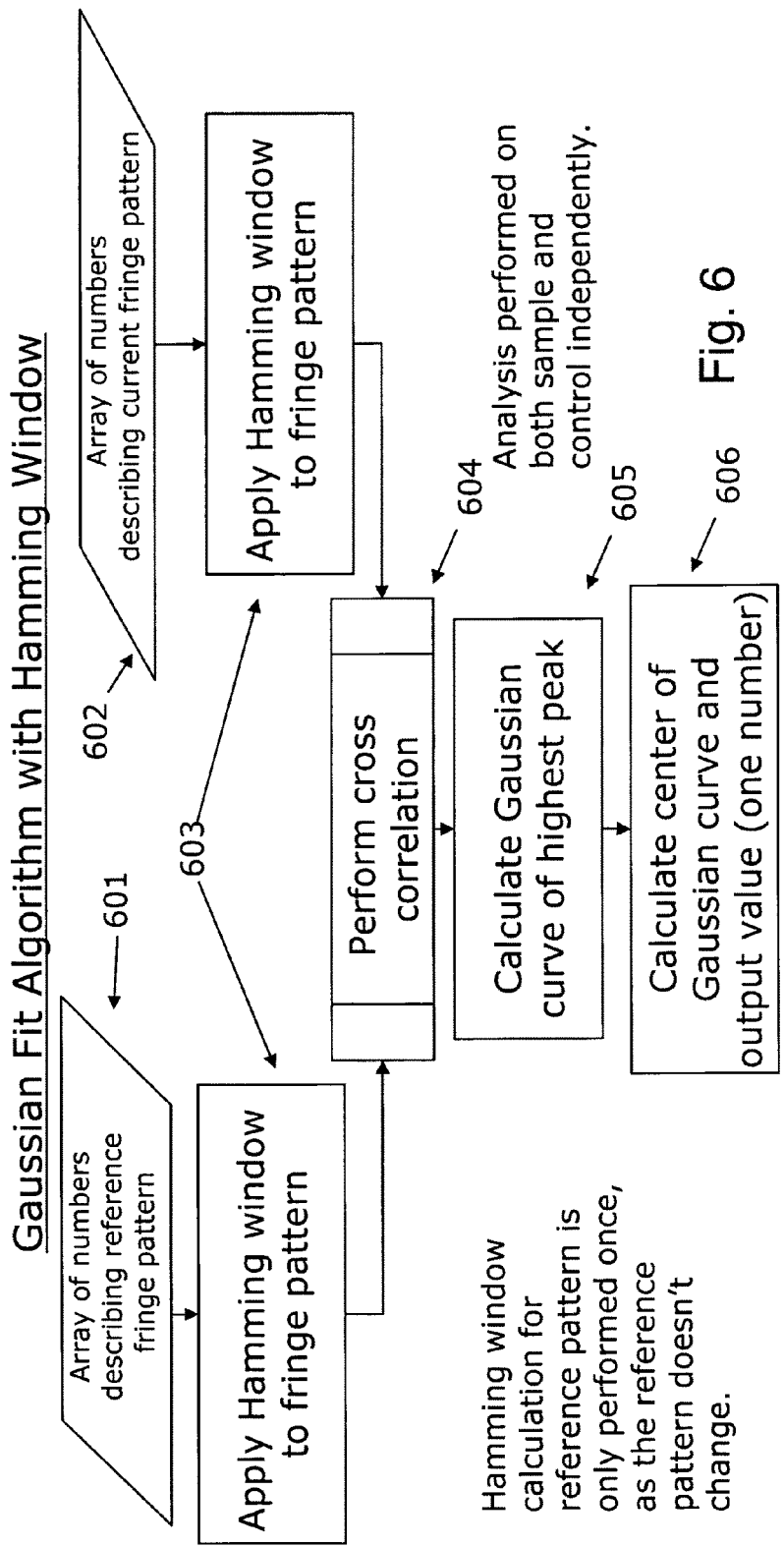
FIG. 6 shows the use of a hamming window.

FIG. 6 shows the use of a hamming window, which is applied to the fringe pattern before the cross-correlation is performed 603. Then a Gaussian fit 605 of the cross-correlation 604 is used to determine the shift in the fringe pattern. The hamming window helps to minimize noise.

BSI can detect changes in refractive index in real time. Therefore, it is a useful tool for measuring binding assays in real time. Also, BSI can be used to compare two samples for differences in refractive index, thereby indicating differences between the contents of the two samples.

Interferometric detection is amenable to high-throughput assay methods, as the molecules, particles or cells do not require labeling with other reagents, such as fluorescent tags, thus requiring less processing of individual samples. The presence of the mass of the immobilized target or a signal due to a binding pair in solution, in embodiments where no binding moiety is immobilized, is detected directly as a function of interferometric fringe position and is robust under laser interrogation. The resulting signal is not susceptible to the photo-bleaching and loss of precision under long or repeated laser exposure of fluorescently labeled targets. Interferometric detection is a sensitive method of detection. Femtomolar or zeptomole levels of numbers of molecules can be detected and low to sub-picomolar (10-12) concentrations of target molecules can be detected.

An analyte can be detected in a sample in a number of ways. First, the interference patterns of a sample and a matched control can be compared. For example, a control sample should contain the same reagents and be contained in a container of the same dimensions as the test sample, but exclude the analyte. In this case, an important element that contributes to differences in the interference patterns will be differences in interaction between the analyte and the reagents in the two samples. For example, in a binding assay, differences between the concentration of an analyte between the two samples will be result in differences in amount of binding with a binding reagent, which, in turn, will result in differences in the interference pattern produced.

However, control and test samples may not be evenly matched. For example, a control plasma sample and a test plasma sample may have differences in various molecules that will result in differences in refractive index even if the concentrations of the analytes are the same. If analyte concentration differences contribute most to differences in refractive index, then this need not be an issue. However, these differences can be addressed in various ways. For example, a kit can provide reagents to construct a standard curve. Measuring results on the test sample against the standard curve provides an indication of the quantity of the analyte in the sample. Comparison of two samples, one with the reagents and one without, provides a measure of what contribution the presence of analytes make to changes in refractive index. A test sample can be divided between two containers, one with reagents and one without, for this purpose. Moreover, for heterogeneous assays which employ sample vessels for which capture molecules have been selectively deposited in given probe regions, sample and experimental measurements can be conveniently performed within a single tube. In this approach, sample of interest is selectively captured using capture molecules prudently localized within the probed region of the sample beam, while the reference beam interrogates a different region of the same vessel, which is devoid of extracted analyte. In this approach sample and reference measurements are performed on the sample matrix solution, variations in biological matrix, such as serological composition, ionic strength, and other bulk propertied can be compensated enhancing the signal to background.

The system can be used to determine the on- and off-kinetics of binding with a flowing system. In the flowing system, one molecule can be attached to the surface with chemistry. A running buffer is then flowed over the activated surface. Once the signal is stable, a second molecule that binds to the first is flown thought the system in increasing concentrations. When the sample interacts with the surface, there is an increase in signal until equilibrium is reached. When the running buffer is flowed back through, the bound molecules disassociate and the signal decreases and then equilibrates on the running buffer. For the reaction of the two molecules, an increase in signal is observed and then equilibrates. For this part of the curve, a 'one phase exponential association' equation is used $[Y=Y_{max}*(1-\exp(-K*X))]$ where K is the K observed. For the dissociation of the two molecules, a decrease in signal is observed until an equilibrium is reached. For this part of the curve, a 'one phase exponential decay' equation is used $[Y=Span*\exp(-K*X)+Plateau]$, where the K is the K off. The K on value is calculated by subtracting the K off from the K observed then dividing the value by the concentration of the binding ligand $\{K_{on}=(K_{obs}-K_{off})/[ligand]\}$. The KD value is collected by dividing the K off by the K on $[KD=K_{off}/K_{on}]$. These equations assume one to one binding and that the concentration of one of the molecules is unchanged during the reaction. This is accomplished by the use of the flow as there is a constant amount of the same concentration being introduced into the channel.

2.6 Instrument with Continuous Injection

Figure 7:
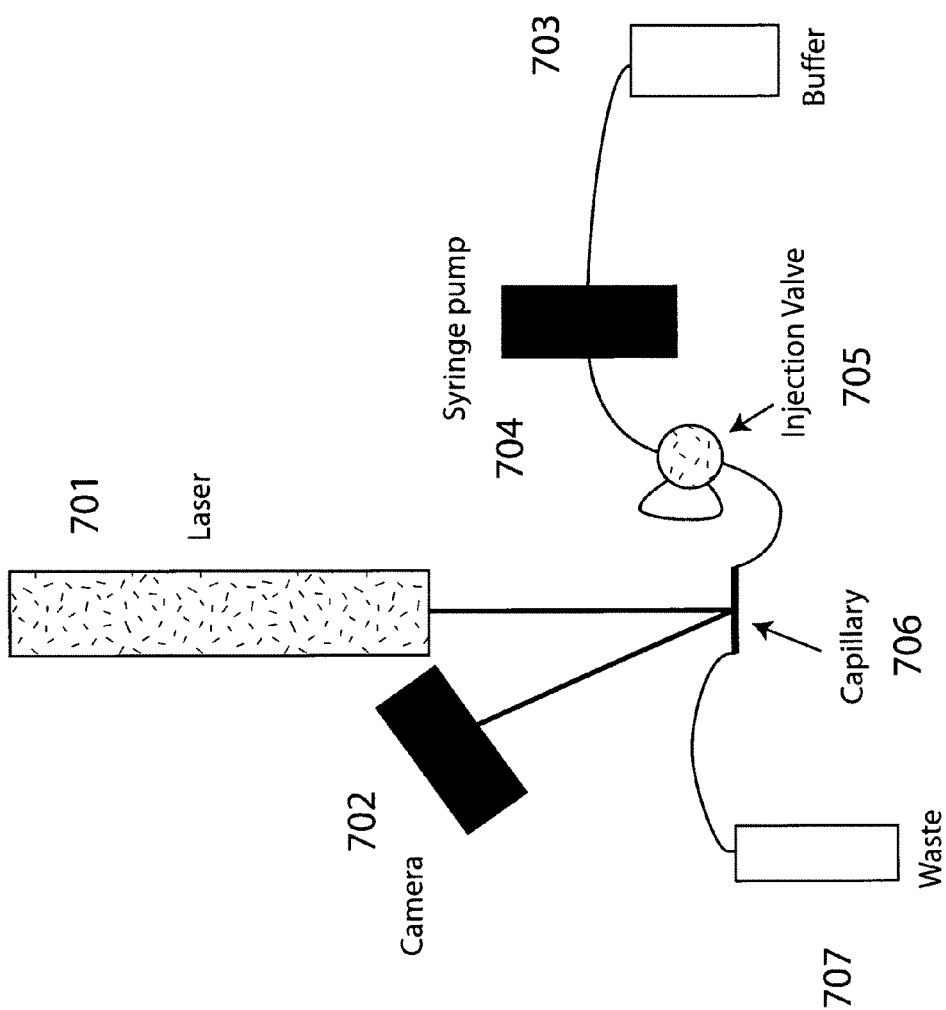
FIG. 7 shows a BSI device for continuous flow-through of sample. The device comprises a syringe pump 704 and injection valve 705.

One version of the instrument allows for sample analysis in flowing streams. (See FIG. 7.) The basics of the instrumentation are the same; a coherent light source 701 is directed onto a fluidic channel 706, which produces a fringe pattern that is captured by a camera 702.

A syringe pump (Cavro) 704 is utilized with an injection valve to create a flowing system. The syringe pump pulls in a volume of liquid from a container 703 which is then dispensed at desired flow rates. These rates can range from 10 microliters per minute to 0.5 microliters per minute, e.g., approximately 2.5 µL/min. The fluid passes through an injection loop and then the detection zone of the instrument. This provides a continuous flow of running buffer in the system. The injection loop can have a volume of 20 µL that can be changed based on the size and length of tubing used. The injection valve 705 allows the injection of different samples without disrupting the flow of the system, as when in the load position the valve circumvents the loop allowing the running buffer to continuously flow. A sample is injected using a 250 µl analytical glass syringe into the loop. When the valve is switched to the inject position, the running buffer flows through the loop, pushing the injected sample into the detection zone. Thus the flow is never interrupted, aside from during the pump refill cycle.

The injected samples are pushed into the BSI instrument, which has a holder, which equilibrates the temperature of the fluid to a set point (typically 25° C.) by wrapping the capillary around a metal bobbin that is temperature controlled. The fluid is then pushed into the detection zone.

The detection zone is a small piece of capillary that the laser strikes. The small section of the capillary allows for surface chemistry to be performed on a large section and then cut into smaller sections for a heterogeneous experiment. After the fluid is analyzed, a waste tube is used to direct the sample into a waste container 707.

3. Detecting Interaction Between Membrane-Bound Components and Analytes 3.1 Introduction One challenge discovered in detecting interactions between membrane components and analytes in a space such as a channel during BSI is that membrane in the sample can dynamically interact with the wall of the container, especially should the container be engineered to support analysis for hydrophilic systems. Under these conditions, a membrane of interest can bind to the wall, be released from the wall, and become denatured during the course of its interaction with the container wall, creating a dynamically changing background signal which produces turbidity and noise that interferes with the sensitivity of detection. This problem becomes more acute as the sensitivity of detection increases. Moreover, this non-ideal membrane behavior represents a stark alteration of its in vivo state, making any empirically derived interaction results susceptible to artifact. The methods of this invention address this issue, among others.

Three methods, in particular, for detecting interaction between a membrane component embedded in a membrane and an analyte are contemplated. One method involves a heterogeneous or tethered format. Two methods involve homogeneous, or in-solution assay formats.

In a first method, which is a heterogeneous assay, a membrane is bound to a surface of a container, such as a microfluidic channel, adapted for analysis by back-scattering interferometry. A fluid containing an analyte to be tested for binding to a component in the lipid membrane is introduced into the container. The amount of binding between the analyte and the component can be determined by back-scattering interferometry.

In a second method, which is a homogeneous assay, a surface of a container is coated with membrane which has no significant affinity for the sample to be analyzed. Such membranes can be control membranes that do not express the binding partner of interest or in the case of a multi-protein complex have been genetically mutated to contain all proteins in the complex except for the binding partner to the sample of interest (e.g., protein). A sample comprising a lipid membrane containing the component (e.g., receptor protein) being tested and the analyte (e.g., target ligand) being tested are introduced into the container. Interaction between the analyte of interest and the non-bound membrane component can be determined by back-scattering interferometry without the need of binding of the membrane bound receptor protein to the surface of the container.

In a third method, which is a homogeneous assay, a first fluid is introduced into a container. The fluid typically will be an aqueous buffer, optionally comprising a detergent that is physiologically compatible with the membrane and with the component selected for testing. A bolus of a second fluid containing the lipid membrane and an analyte to be tested is introduced into the compartment under conditions creating laminar flow. If the speed of flow is sufficiently fast, such that the leading edge of the bolus that contains the lipid membrane does not completely displace the first fluid and the lipid does not bind to the surface in quantities sufficient to create a noise signal that significantly interferes with the signal from bolus, a binding signal between the membrane component and analyte can be measured. The binding signal between the membrane component and the analyte is preferentially monitored during this period before the test fluid has displaced the first buffer or created a noisy signal.

3.2 Lipid Membranes

This invention provides methods for detecting interactions between components associated with lipid membranes and various analytes. The membranes used herein may be synthetic or naturally occurring, for example, but not limited to, vesicles, liposomes, monolayer lipid membranes, bilayer-lipid membranes, membranes incorporated with receptors or the like. Membranes suitable for use with the present invention are amphiphilic molecules, for example, but not limited to, phospholipids, sphingomyelins, cholesterol or their derivatives. In a preferred embodiment, the membrane is a bilayer-lipid that is derived from or simulates a natural cell membrane and may be of varied lengths.

The membrane typically includes a membrane component, e.g., a protein, whose binding characteristics are the object of study. Membrane proteins include peripheral membrane proteins, integral membrane proteins and lipid-anchored proteins. Peripheral membrane proteins are proteins that adhere only temporarily to the biological membrane with which they are associated. These molecules attach to integral membrane proteins, or penetrate the peripheral regions of the lipid bilayer. The regulatory protein subunits of many ion channels and transmembrane receptors, for example, may be defined as peripheral membrane proteins. Examples include ionophores (for example, but not limited to, valinomycin, nonactin, methyl monesin, coronands, cryptands or their derivatives), ion-channels (for example, but not limited to, protein ionophores, etc.) An integral membrane protein is a protein molecule (or assembly of proteins) that is permanently attached to the biological membrane. In lipid-anchored proteins, a covalently attached fatty acid such as palmitate or myristate serves to anchor them to either face of the cell membrane. Examples include G proteins and certain kinases. It is believed that the fatty acid chain inserts and assumes a place in the bilayer structure of the membrane alongside the similar fatty-acid tails of the surrounding lipid molecules.

3.2.1 Preparation of Membranes

Solutions comprising membranes from cells for use in any of the methods described herein can be prepared by any method known in the art. For example, the cells will be any cells whose membranes contain a component to be analyzed. These can be cells from cell culture or from organisms. Tissue or cells are solubilized in an appropriate buffer, cleaned and isolated, e.g., by centrifugation. The isolated cells are mixed with a buffer comprising a detergent that will aid fragmentation of the membrane but will not remove the component of interest from the membrane. The cells are fragmented by homogenization, sonication, shearing, other mechanical methods or similar methods. Membrane materials are washed and isolated, e.g., by centrifugation. Then the membranes are re-suspended in appropriate buffer. Sample protocols for preparing membranes are provided in the Examples.

Membranes typically will be maintained in a buffer that is compatible with maintaining an intact membrane and biological activity of the component being tested. For example, the buffer can be around pH 7, for example, between pH 6.5 and pH 8.5. The buffer can contain a detergent, such as Triton (e.g., Triton X-100, Triton X-200, etc.), Tween and octyl-beta-D galactopyranoside. The buffer can comprise a protease inhibitor. Useful buffer systems include PBS, PIPES, MOPS, TES, HEPES, Trizma, Tricine and CAPSO. The nature of the component being analyzed also is a consideration in the selection of the buffer. For example, peripheral membrane proteins are loosely bound to the membrane surface. Therefore, less harsh buffers are more useful for this system.

One also can obtain membrane material commercially. This includes membranes from specific cell types, such as CHO cells or liver cells, and membranes from cells engineered to over-express membrane proteins. For example, Perkin Elmer (Waltham, Mass.) offers for sale GPCR membrane preparations, ion channel membrane preparations, transporter membrane preparations, tyrosine kinase membrane preparations, and wild-type control membrane preparations.

3.3 Analytes

The assays of this invention are useful for determining interaction of various analytes with membrane-associated components. Such assays are useful in drug discovery in which drug candidates are tested for their ability to bind the component of interest. They also are useful to test interaction of membrane-bound components with their naturally occurring binding partners. Components can be tested in membranes in which they exist at nascently low amounts, e.g., native membranes. BSI is particularly useful to perform the assays of this invention as it can detect interactions at very low concentrations and, therefore, provides a very sensitive assay.

Analytes that one can test include, without limitation, small organic molecules, biopolymers, macromolecular complexes, viruses and cells. Drug candidates useful as analytes in this invention include small organic molecules and biological molecule, e.g., biologics. Organic molecules used as pharmaceuticals generally are small organic molecules typically having a size up to about 500 Da, up to about 2000 Da, or up to about 10000 Da. Certain hormones are small organic molecules. Organic biopolymers also are used as analytes. These include, for example, polypeptides (e.g., peptides and proteins), polynucleotides (e.g., oligonucleotides or nucleic acids), carbohydrates, lipids and molecules that combine these, for example glycoproteins, glycolipids and lipoproteins. Certain hormones are biopolymers. Antibodies find increasing use as biological pharmaceuticals. U.S. publication 2009-0035216 provides a list of antibody drugs. This list includes, for example herceptin, bevacizumab, avastin, erbitux and synagis (cell adhesion molecules). Macromolecular complexes also can be used as analytes. They are typically at least 500K Da in size. They include, for example, membrane complexes that are macromolecular assemblies like ion channels and pumps (e.g., Na—K pumps), ATP-ases, secretases, nucleic acid-protein complexes, polyribosomal complexes, polysomes, the p450 complex and enzyme complexes associated with electron transport size. Viruses and parts of viruses e.g., capsids and coat proteins, also can be analytes. Cells can be analytes. In this way, for example, cell surface molecules, such as adhesion factors, can be tested. Cells can be, for example, pathogens, cancer cells, inflammatory cells, t-cells, b-cells, NK cells, macrophages, etc.

3.4 Assays

In performing an assay in this system, a device having a compartment with a lipid-like layer is provided. A solution comprising the lipid membrane being tested is introduced into the compartment under conditions that allow the membrane to adhere to the lipid like layer. A solution comprising the analyte being tested is then introduced into the compartment. The temperature of the compartment can be regulated using a temperature regulator, such as a peltier device. The compartment can be interrogated by a laser continuously or after the fluid with the analyte has been allowed to enter the channel and equilibrate. Continuous measurement provides a baseline against which the test can be measured. Interaction between the analyte and the membrane component can be determined by comparison with a control sample that does not include the analyte, or that contains an analyte known not to be bind with the membrane component.

3.4.1 Creation of Lipid-Like Layer on Compartment Surface

In certain embodiments, this invention involves creating a lipid-like layer on the internal surface of the compartment that is to be interrogated. Lipid membranes can be attached to the compartment wall covalently or non-covalently. One method of non-covalent binding involves immobilizing a lipid-like layer to the internal surface of the channel and using this layer to bind the lipid membrane being tested.

A lipid-like layer can be formed on a surface of a compartment wall by any method known to couple molecules to a surface. One method involves attaching bifunctional linkers to the surface and then attaching the molecule having a lipid-like portion to the free functional group of the bifunctional linker. Such methods are described, for example, in U.S. Pat. No. 7,045,171 (Bookbinder).

In order to create a surface in the fluidic channel that is lipid like, one can create a surface that comprises large linear or branched aliphatic chains. Using surface chemistry that is based on primary amine binding, it is possible to bind a hydrophobic molecule like hexadecylamine to the surface where a hydrophobic surface would be created. For example, 3-mercaptopropyltriethoxysilane and N-(γ-maleimidobutyryloxy)succinimide ester is used to create the initial surface layer on the fluidic channel, which then interacts with the primary amine of a long chain alkyl amine. A variety of chain lengths exists which can be bound to the channel surface and experimentation can be performed to optimize the chemistry for the membrane. Also these long chains are insoluble in water and must be dissolved in a solvent that is favorable to the previous surface chemistry (in ethanol for example). Once the long chain alkyl amine layer is created it is possible to bind the membrane to the surface of the channel.

3.4.1.1 Surface Modification

In certain methods, surfaces are prepared for attachment with a lipid-like layer by modifying the surfaces with bifunctional coupling agents, that is, reagents bearing reactive groups at both termini. One end is used to attach to the surface. The other end is used to attach to a molecule having a lipid-like quality.

For some embodiments of the invention, the chemical moieties on the substrate surface which are amenable to chemical modification are hydroxyl groups. For example, glass substrates present a population of hydroxyl groups. The density of these hydroxyl groups depends on the handling and storing conditions to produce the glass substrate. A number of other substrates also exhibit hydroxyl groups as usefully modifiable chemical moieties on the surfaces of those substrates. Other chemically modifiable groups may include, but are not limited to sulfides, sulfhydryls, amino groups, boronates, carboxylates, and the like.

In plastic substrates, surfaces can be oxidized using corona or plasma discharge, creating a covalently attached oxidized layer with associated hydroxyl groups for subsequent coupling via bifunctional agents.

The substrate is cleaned in preparation to applying a layer to it. In some embodiments, the cleaning step comprises chemical treatment which will induce the formation of chemically modifiable groups on the substrate surface, for example, the introduction of oxide groups on a metal surface. Alternatively, corona or plasma discharge can be used.

3.4.1.2 Reagents for Covalent Modification of the Substrate Surface

The reagent bearing reactive groups at both termini is used to functionalize the chemically modifiable groups already present on the substrate surface, by reacting at one of the two termini with the chemically modifiable group on the substrate surface, and retaining the second reactive group for further reaction with a polymer or other species that will act to modulate the nonspecific binding and/or be capable of further modification to induce specific binding of the target molecule, particle, or cell. The reactive group still present at the second terminus is often more reactive than the chemically modifiable group on the original untreated surface and can therefore react with a wide variety of chemical species to introduce surface modification which will modulate nonspecific binding and/or be capable of inducing specific interactions of desired molecular species with the substrate.

Examples of the reagent bearing reactive groups at both termini to initially modify the substrate surface for use in the present invention include, but are not limited to, isocyanates (e.g., toluene diisocyanate), silanes, methacrylates, disulfides, disilazanes, sulfhydryls, acrylates, carboxylates, activated esters, other active leaving groups, isonitriles, phosphoamidites, nitrenes, epoxides, hydrosilyl, esters, arenes, azido, amine, nitrile, vinyl groups, alkylphosphonates, and other surface-coupling reactive species known to those skilled in the art of chemical coupling to surfaces. In some embodiments, the reagent bearing reactive groups at both termini bears at least one silane group, a group selected from a methacrylate group, a disulfide group, a disilazane group, a sulfhydryl group, a acrylate group, a carboxylate group, an activated ester group, an active leaving group, an isonitrile group, an isocyanate group, a phosphoramidite group, a nitrene group, an epoxide group, a hydrosilyl group, an ester group, an arene group, an azido group, an amino group, a nitrile group, a vinyl group and an alkylphosphonate group. The reactive groups at both termini may be the same or different.

In one embodiment, a surface having free hydroxyl groups is washed with 10% (w/w) potassium hydroxide in methanol. The surface is then derivatized with tri-alkoxy silane having an alkyl group and a reactive group at a second terminus. For example, the compound can be mercapto propyl triethoxy silane in toluene. In certain embodiments, the reactive group at the second terminus can be directly coupled to the molecule bearing the lipid-like moiety. Alternatively, the reactive group at the second terminus can be converted into another reactive group that will be coupled to the molecule. For example, the free thiol group described above can be reacted with a maleimide succinic esther to generate a thioesther group. For example, the reactant can be N-(γ-maleimidobutyryloxy)succinimide ester in ethanol. The reactive thioesther group can react with a molecule comprising a lipid-like moiety, e.g., a hydrophobic, moiety.

3.4.1.3 Molecules with Lipid-Like Moiety

A molecule comprising a lipid-like moiety is then attached to the available reactive group of the bifunctional linker already attached to the surface to provide a hydrophobic surface that has affinity for lipid membranes. Typically these molecules comprise a reactive group, such as an amine, to bind with the available reactive group on the linker and a lipid-like moiety. In certain embodiments, the molecule comprises a hydrophilic linker that attaches the lipid-like moiety to the bifunctional linker. However, in other embodiments, the lipid-like molecule does not have a hydrophilic linking moiety.

The reactive moiety can be any moiety that reacts with the available functional group on the bifunctional linker to produce a covalent bond. In some embodiments the molecules having a lipid-like moiety are attached to the bifunctional linker through a thiocarbamate bond, a carbamate bond, a urethane bond (e.g., through reaction with an isocyanate), an amide bond, a guanidinium bond, an ether bond, a sulfide bond or a disulfide bond.

The lipid-like moiety typically has a high hydrophobic index. In one embodiment the membrane binding moiety or "hydrophobic tail" of the lipid-like molecule can be hydrophobic or amphiphilic with straight or branched chain alkyl, alkynyl, alkenyl, aryl, araalkyl, heteroalkyl, heteroalkynyl, heteroalkenyl, heteroaryl, or heteroaraalkyl. The lipid-like region that binds to the membrane can comprise a C10 to C25 straight or branched chain alkyl or heteroalkyl hydrophobic tail. For example, the lipid-like moiety comprises a C10 to C20 straight or branched chain alkyl fragment. For example the lipid like moiety could comprise a long chain (e.g., C10 to C25) alkyl such as a C16 alklyl. They may comprise a primary amine group to react with the lipid like moiety. For example, the lipid-like molecule could be hexadecyl amine. Long aliphatic chains are insoluble in water and must be dissolved in a solvent that is favorable to the previous surface chemistry, for example, ethanol.

In other embodiments, the link can be a non-covalent link in which the groups have a tight binding affinity, such as a chelating group and metal ion.

3.4.2 Heterogeneous Assay: Membrane Bound to Compartment Wall

In one embodiment, lipid membrane is immobilized to the compartment wall in a way that allows the membranes to bind to the surface of the channel without denaturation. A fluid comprising an analyte for testing with the membrane component of interest is flowed through the compartment. The binding of these substances to the membrane can then be monitored. The binding of the membranes to the surface could either be from the inside or outside of the membrane, so binding of the substance to the membrane can be on either side.

A channel comprising a lipid like layer as described above can be provided. Then, a membrane preparation is contacted with the lipid like layer. Because the lipid like layer has affinity for the membrane, the membrane sticks to the layer. Once the channel is prepared, the preparation of experiments is set up in a heterogeneous fashion. A varied concentration of the substance that interacts with the membrane is introduced in increasing concentration. The rinsing buffer must be set up so that the membranes are in a favorable environment.

This fluidic channel setup would allow for either stop flow or flowing experimental configuration. In the stop flow experiment, the increasing concentration of samples would provide increasing signal strength until saturation is reached. The binding affinity can then be calculated based on a one site binding hyperbola. In the flowing system, monitoring of the Kobs (one phase exponential association) and Koff (one phase exponential decay) for each concentration would allow for Kd calculations.

In both the flowing and stop flow experiments, correct controls must be analyzed. In this case, the control can be a fluidic channel that has not been surface activated. Preferentially, a control membrane that has no reactivity for the substance being analyzed can be bound to the surface.

3.4.3 Homogeneous Assay: Compartment Wall Passivated with Hydrophobic Layer

In one version of a homogeneous assay, the surface is either solely modified with the poly aliphatic coating, or can more aptly be modified by binding a passivating membrane to the polyaliphatic chain as described above. The lipid-like layer can be provided on the compartment surface as described above. The passivating membrane is a cell membrane or membrane mimetic which does not contain the targets of interest. After introduction, it binds to the lipid like layer and prevents sticking by active membrane subsequently introduced. The assay proceeds as all other homogeneous BSI assays are performed, with both control and assay samples being pre-incubated prior to introduction to the treated chip. In this method, the solution comprising the membrane and the analyte to be tested are mixed together before introduction into the compartment.

3.4.4 Homogeneous Assay: Laminar Flow Environment

When a fluid comprising lipid membrane material is passed through a channel, the membrane material can become bound to the inside wall of the channel through a variety of non-covalent forces. In the context of back-scatter interferometry, such sticking produces noise that interferes with the sensitivity of detection of the interference fringe pattern and changes in its position as the refractive index of the fluid changes. The laminar flow method of this invention addresses this issue.

Figure 2:
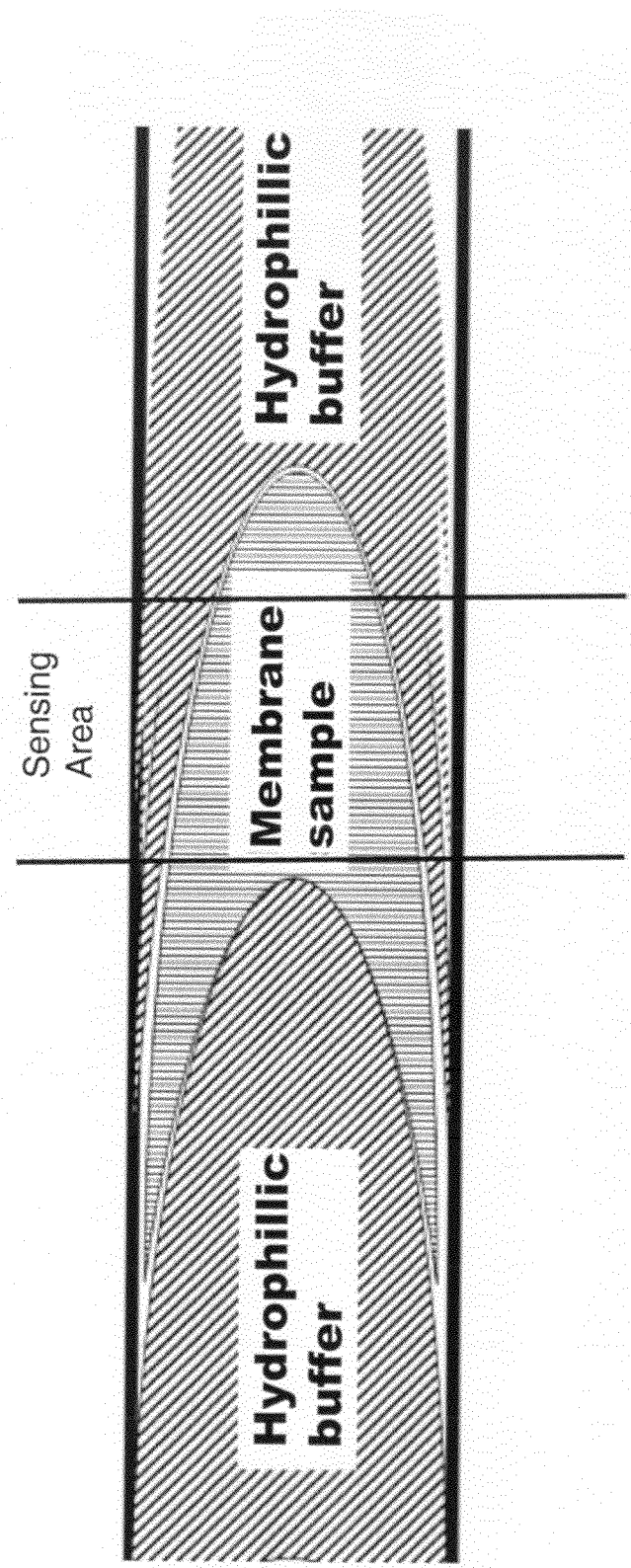
FIG. 2 shows a channel comprising a sensing area. Two liquids are flowed through the channel so that a bolus of the second liquid does not completely displace the first liquid in the sensing area. Measurements can be taken during this time.

The character of the motion of fluids is determined by factors including the linear velocity of the fluid and the viscosity of the fluid. The Reynolds number is a parameter that indicates whether flow will be laminar, unstable, or turbulent. Laminar flow occurs when fluids travel with a Reynolds number of less than 500, and creeping motion or Stokes flow motion occurs when the Reynolds number is less than one. When liquids flow through channels under laminar flow conditions, the linear velocity of the fluid decreases radially from the center toward the edge of the flow. Thus, if a second liquid follows a first liquid into a channel under laminar flow conditions, the center portion of the second liquid will flow ahead of the first liquid located near the channel wall. Accordingly, the second liquid will from a bullet shape bounded around its edge by the first fluid. At this stage, the second fluid will not have completely displaced the first fluid in the channel. (See FIG. 2.)

Another aspect of fluids moving in a channel is radial diffusion. Materials concentrated toward the center of the flow will diffuse outward. However, depending on the rate of that diffusion and the linear velocity of the liquid, material, such as lipid membrane, in the bullet portion of a second fluid traveling within a first fluid under laminar flow conditions, the amount of the material that reaches and adheres to the wall of the channel can be limited.

According to the present method, a first fluid is introduced into a channel. The fluid preferably is a buffer having a pH that is compatible with the functioning of the membrane component being tested. The fluid also can comprise a detergent. Such buffers and detergents are described above.

A second fluid that contains lipid membrane containing the component for test is introduced into the channel under laminar flow conditions and at a speed so that there is no significant radial diffusion of membrane component to the wall of the channel during sensing. A portion of the compartment, designated as the sensing area or detection zone, is positioned so that the head of the bullet, which is surrounded by the first fluid, passes through the sensing area. A period after the first fluid enters the sensing area and before the first fluid completely fills the sensing area and displaces the second fluid is designated as the detection period. Back-scatter light is generated and detected during this detection period. The linear flow rate of the liquid preferably is between about 0.2 mm/sec and about 3.5 mm/sec.

4. Examples

4.1 Membrane Preparation for In Vitro Enzymatic Assay

Two protocols for preparation of membrane for assays or for passivation are presented.

4.1.1 First Protocol

For preparation of cell membranes, cells were harvested from confluent 850-$cm^2$ roller bottles by treatment with PBS-EDTA and centrifugation at 500×g for 5 min. The cell pellet was resuspended in homogenization buffer ((mM) HEPES 20, EDTA 1, [ethylene-bis(oxyethylenenitrilo)]tetraacetic acid (EGTA) 1, $MgCl_2$ 6, pH 7.4) and the cells left to swell on ice for 20 min before homogenization in a Waring blender (3×15 s, with 2 min incubation on ice between each bout). The homogenate was centrifuged at 1000×g for 10 min and the resulting supernatant was centrifuged at 48,000×g for 20 min at 4° C. The supernatant was discarded and the pellet was resuspended in 5 ml homogenization buffer per roller bottle. The membrane suspension was then frozen in aliquots at −80° C. until required.

4.1.2 Second Protocol

In another embodiment, for buffers, one can use 10 mM Tris with 2 mM EDTA at pH 7.5. Additionally the same buffer may be made without the EDTA. A sugar buffer with 20 mM Tris with 0.5 mM EDTA and 0.1 M NaCl in water with 0.139 M sucrose is made. A 20 mM Tris with 0.5 mM EDTA and 0.1 M NaCl in water (without sucrose) is made for dilution purposes.

A 0.1 M DTT and add 100 μL to 10 mL of 10 mM Tris and 2 mM EDTA is made. A 40 mM NEM in 20 mM Tris (NEM—N-Ethylmaleimide) is made. For the use of protease inhibitors, make 400 mM and use at 1% final concentration.

For the procedure, aspirate the media then wash once with 10 mL PBS. Add 1 mL PBS and scrape cells onto tubes. Repeat addition of PBS and scrape if necessary. Make sure to wash the scraper to avoid contamination. Centrifuge to pellet cells for 1 minute.

Lyse cells in 10 mM Tris with 2 mM EDTA and 1 mM DTT and then wash twice with above solution and resuspend in 200 uL. Add 1:1 with 40 mM NEM in Tris and incubate on ice for about 20 minutes.

Wash twice with 10 mM Tris with 2 mM EDTA. Resuspend in 400 μL of above buffer and 4 μL of protease inhibitors. Keep on ice for an hour with vortex and homogenization every 15 minutes. (Set centrifuge tubes and holders on ice.)

Put through a 26.75 g needle six times. Place 500 μL 60% sugar, then place sample on top into centrifuge tubes. Balance the tubes and spin at 38,000×g for 30 minutes in a swing-out rotor. Take the membrane fraction in between the top fraction and the 60% sucrose layer (about 300 μL).

Remove the rest of the liquid and re-suspend into a suitable buffer. Dilute membrane fraction at least six times in 20 mM Tris with 0.5 mM EDTA and 0.1 M NaCl in water. Spin at 100,000×g for 15 minutes. Re-suspend in a volume of 20 mM Tris, 0.1 M NaCl with inhibitor.

4.2 Bradykinin Model System

To demonstrate the methodology and steps involved in a heterogeneous assay, we utilize components from a commercially available bradykinin—B1 and B2 membrane receptor system. The nonapeptide bradykinin (BK) and Lys-BK (kallidin) are naturally occurring substances produced by the proteolytic digestion of high or low molecular weight kininogen by plasma and tissue kallikrein, respectively, following a suitable stimulus in most species.

T-kinin (Ile-Ser-BK) is formed from T-kininogen in the rat. Removal of the C-terminal arginine of BK and Lys-BK by carboxypeptidases generates the peptides BK (1-8), also referred to as [des-Arg9]-BK, and Lys-BK (1-8), also known as [Lys-des-Arg9]-BK or [des-Arg10]-kallidin, respectively.

Bradykinin and the related kinins possess a wide range of pharmacological actions and are believed to be important mediators of pain and inflammation and to be involved in the control of local blood flow. Kinins induce their effects via two main types of receptor, designated B1 and B2, both of which belong to the superfamily of G protein-coupled receptors. However, a third receptor designated B3 has been proposed based on variation in affinity or inactivity of antagonists.

Bradykinin and Lys-BK are relatively selective ligands at the B2 receptor whereas BK (1-8) and Lys-BK (1-8) are selective ligands at the B1 receptor. BK (1-8) is a more potent agonist at the rodent/murine B1 receptor as compared with its activity at the human B1 receptor for which the B1 agonist of choice is Lys-BK (1-8).

The B2 receptor is generally present in a wide variety of tissues. In contrast, the B1 receptor is not normally present, but is up-regulated over a period of several hours both in vitro and in vivo following exposure to noxious stimuli such as LPS and other inflammatory mediators such as IL-1, IL-2 and growth factors such as EGF.

The molecular cloning of cDNAs encoding the kinin receptors has provided direct evidence for the existence of B1 and B2 receptors as the products of distinct genes. The human, dog, mouse and rat B2 and B1 receptors have been cloned, expressed, sequenced and characterized pharmacologically. Human and rabbit B1 receptors, respectively, exhibit approximately 2,000- and 150-fold higher affinities for Lys-BK (1-8) relative to BK(1-8) whereas the mouse B1 receptor exhibits a 2-3 fold higher affinity for BK(1-8) compared to Lys-BK(1-8). The homology between the human B2 and B1 receptor sequence is only 36% at the amino acid level. In comparison, the human B1 receptor is 30% identical to the AT1 angiotensin II receptor.

Many cells co-express both B1 and B2 receptors and in the majority of cases when stimulated they mediate responses in the same direction. However, subtle differences have been noted in cells that co-express both receptors that may reflect molecular and physiological differences between B1 and B2 receptors. For example, the increase in intracellular calcium is more persistent, less susceptible to tachyphylaxis, and less inhibited by nickel ions when elicited by B1 receptor activation as opposed to B2 receptor stimulation in bovine pulmonary arterial cells. In addition, internalization of B1 ligand receptor complexes fails to occur in the rabbit aorta smooth muscle cell binding assay.

Activation of both the B1 and the B2 receptor has been implicated in many pathophysiological disorders and efforts have been made to develop selective agonist and antagonist ligands for both receptors for use as pharmacological/biochemical tools and potential therapeutic agents. In addition, there is a belief that blocking both receptors may be beneficial in certain circumstances, such as hyperalgesia, and peptide-based compounds have been developed that display high affinity for both receptors (e.g., CP-0364 and B9430). Mice lacking the B1 or B2 receptor are available and are helping with our understanding of these receptors in development, and in normal and altered physiology. Finally, with respect to B2 receptor antagonists, these can be divided into first generation (e.g., D-Arg [Hyp3,Thi-5,8,D-Phe7]-BK), second generation (e.g. HOE 140 and NPC 17731) and third generation (e.g., the non-peptides, FR 173657 and bradyzide).

This assay makes use of the following commercially available reagents: Bradykinin B1 Receptor PerkinElmer Product number ES-091-M400UA. MEMBRANES: 1×400 units/1000 μl frozen aliquot. PACKAGING BUFFER: 50 mM Tris-HCl pH 7.4, 0.5 mM EDTA, 10 mM MgCl2, 10% sucrose STORAGE CONDITIONS: Store at −80° C. Avoid repeated freeze-thaw. UNIT SIZE: 50 μg protein/unit. EXPRESSION LEVEL (BMax): 0.24 pmol/mg membrane protein. PROTEIN CONCENTRATION: 20 mg/ml.

4.3 Experiment 1

Heterogenous Assay with Membrane Bound to Channel Surface 4.3.1 Creation of Lipid-Like Layer for Attachment of Membrane A capillary tube was prepared having a lipid like layer comprising hexadecyl alkane groups attached to the bore cavity through propyl-ethoxy silane groups as described above. A capillary tube was washed with 10% (w/w) potassium hydroxide in methanol. The surface is then derivatized with mercapto propyl triethoxy silane in toluene. The free thiol group was reacted with a N-(γ-maleimidobutyryloxy) succinimide ester in ethanol. The reactive thioester group was reacted with hexadecyl amine to provide the lipid-like layer. The running buffer (50 mM Tris with 5 mM MgCl2) is flowed through the capillary until the signal stabilizes.

For the assay capillary the human Bradykinin B1 Receptor membrane fraction is then flown into the capillary at approximately 10 mg/mL and a change in signal is observed. The running buffer pushes out the membrane and a change in the baseline from the buffer is observed, demonstrating the binding to the lipid like surface. For the control capillary, the CHO cell membranes are injected and again a change in the baseline for the buffer is observed.

4.3.2 Performance of Assay

Experiment Workflow for BSI Experiment
1. Buffer was prepared, 50 mM Tris-HCl, pH 7.4, 5 mM $MgCl_2$, using high quality grade reagents from Sigma Aldrich. The buffer was filtered and degassed before use.
2. Capillary was prepared with KOH, MEPTES, GMBS & Hexadecylamine as described above.
3. The capillary was equilibrated in above buffer.
4. 50 µl of membranes containing the bradykinin B1 receptor protein were injected without dilution (as supplied by manufacturer).
5. The capillary was washed in the above buffer.

The peptide tested against Bradykinin $B_1$ membrane bound receptor was Lys-(Des-Arg$^9$)-Bradykinin/Lys-(Des-Arg$^{10}$)-kallidin (Sigma), molecular weight=1032.20. A concentration range of this peptide was made by serially diluting the peptide in the above buffer to give final concentrations of 50 nM, 25 nM, 12.5 nM, 6.25 nM, 3.125 nM, 1.56 nM, 0.78 nM, 0.39 nm, 0.195 nM, 0.097 nM, 0.048 nM, 0.024 nM, 0.012 nM, 0.006 nM & buffer alone as a blank.

6. With the baseline stable after step 5, the Lys-(Des-Arg9)-Bradykinin was injected with increasing concentrations. As the molecule binds to the membrane, an increase in signal occurs. As the running buffer enters the detection zone the signal decreases.
7. For the control capillary, the control CHO cell membranes were injected neat without dilution (as supplied by manufacturer).
8. The capillary was washed in the above buffer.
9. With the baseline stable after step 8, the Lys-(Des-Arg9)-Bradykinin was injected with increasing concentration. The same series of concentrations as made in step 6 were used. Any bulk refractive index change will result in a similar binding curve as the assay membrane (though less magnitude).
10. The signal for the control at each analyte concentration is subtracted from the signal of the assay at each analyte concentration. The resulting curve allows for the determination of Kobs and Koff as described elsewhere in this document.

4.3.3 Results

The combined data is the results from each concentration (control subtracted from the assay for each concentration). The data shows that with increasing concentration, there is an increased signal, indicating binding. As the sample starts to interact with the membrane, the signal increases. As the running buffer pushes the sample out, the bound sample is then washed off showing a decrease in signal.

Figure 8:
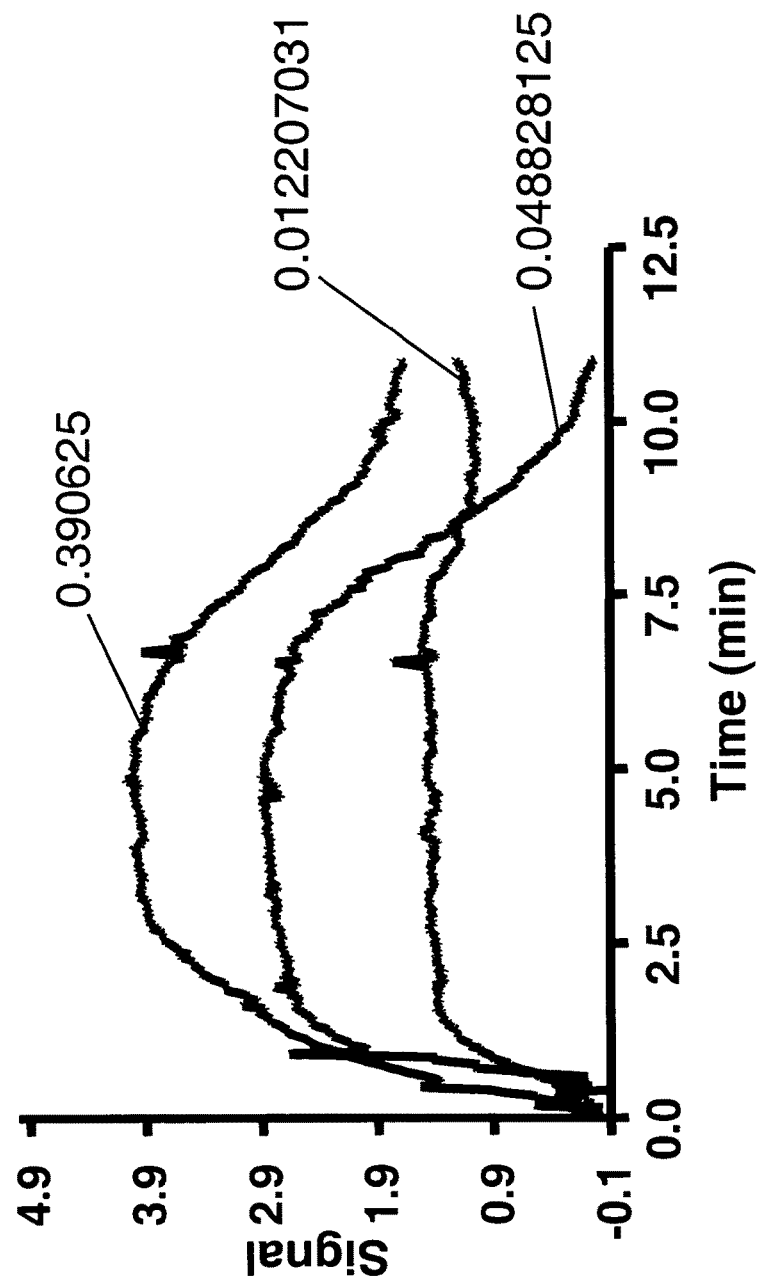
FIG. 8 shows time course results for Experiment 1, a heterogenous assay.
Figure 9:
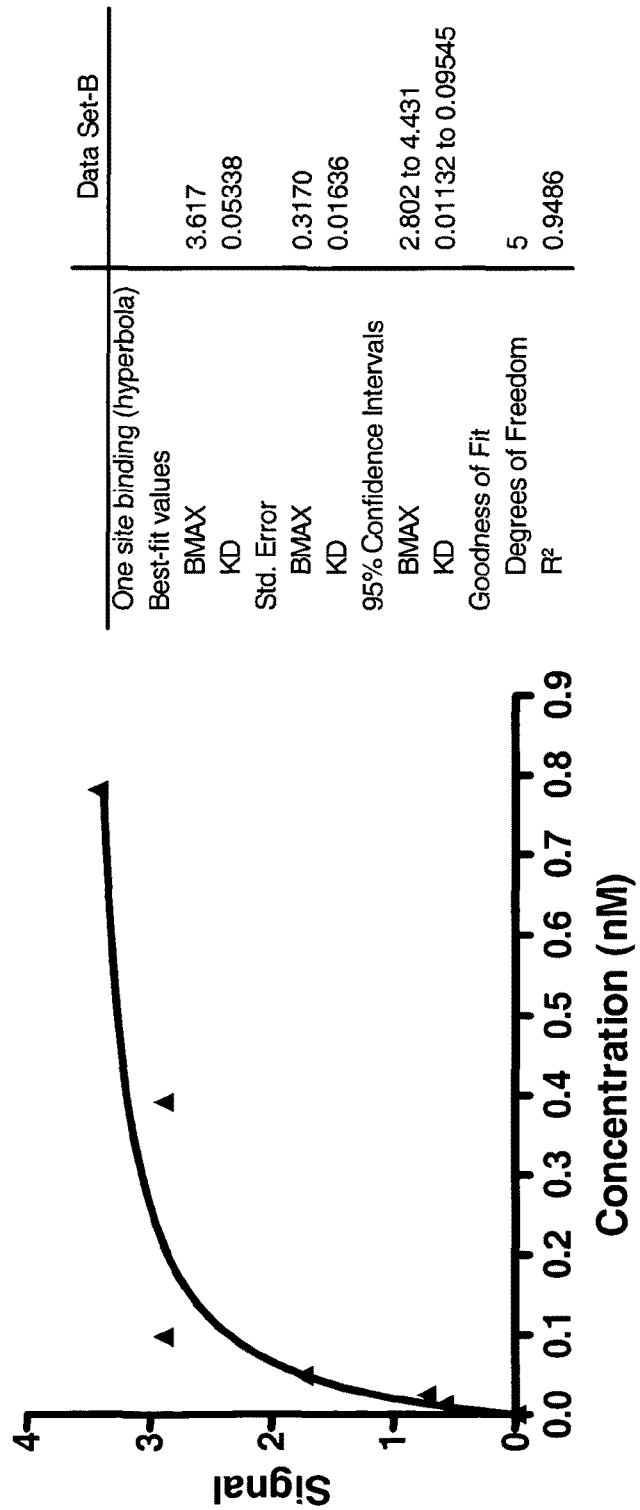
FIG. 9 shows the endpoint analysis results for Experiment 1.
Figure 10:
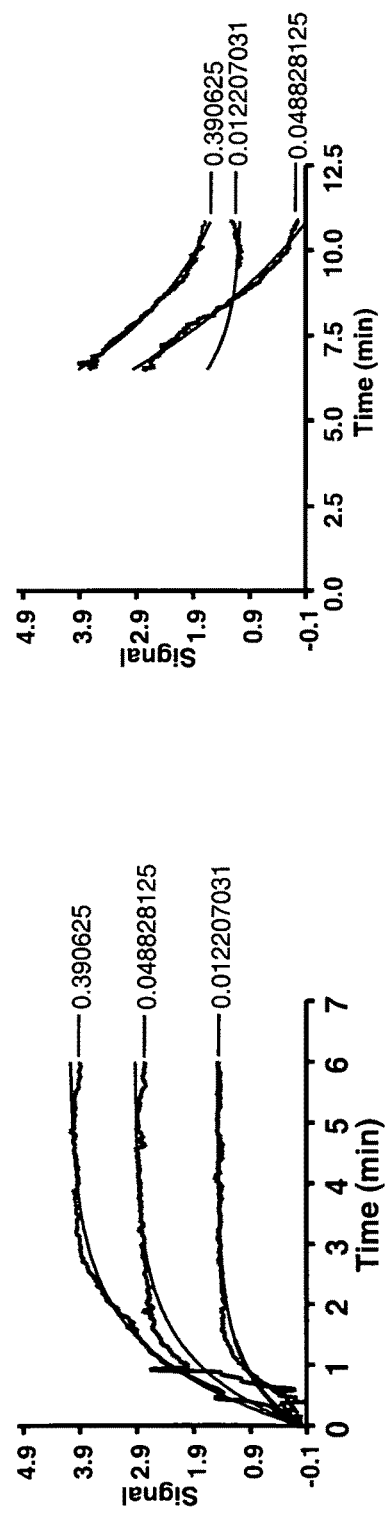
FIGS. 10A and 10B shows the Kobs and Koff results for Experiment 1.

FIG. 8, FIG. 9, and FIG. 10 show the results of the assay. As can be seen in FIG. 8, with increasing concentration, there is an increased signal, indicating binding. As the sample starts to interact with the membrane, the signal increases. As the running buffer pushes the sample out, the bound sample is then washed off showing a decrease in signal. In FIG. 9, the maximum from each of the concentrations is plotted versus the concentration. This is an endpoint analysis that has a one site binding fit, which produces a value of 0.053 nM. In FIG. 10 the data from FIG. 8 is split into the Kobs and Koff. The value of Kd is calculated as described in section 2.5 and is 0.41 nM.

4.4 Experiment 2

Homogeneous Assay with Passivated Surface 4.4.1 Creation of Passivated Surface The passivated surface is prepared as follows. A surface comprising a lipid-like layer is made using the same protocol as described above for the heterogeneous assay in (experiment 1) section 4.2.1.

Then, a control membrane preparation (one that will not bind the target analyte) is bound to the surface, again as described above for creating the surface for the heterogeneous assay. This surface is used for the experiments.

4.4.2 Performance of Assay

The interaction of the Lys-(Des-Arg9)-Bradykinin and the membranes are set up in a homogeneous manner. The Lys-(Des-Arg9)-Bradykinin is serially diluted to 50 nM to 6 pM and then split. The membranes are diluted to 20 µg/mL and then mixed 1:1 with one set of the split Lys-(Des-Arg9)-Bradykinin concentrations. Concentration of the samples and membranes are therefore halved to 25 nM to 3 pM and 10 µg/mL respectively. The mixture was then allowed to incubate for six hours. Buffer was added 1:1 to the other set to form the controls without the analyte.

The running buffer (50 mM Tris with 5 mM MgCl2) was flown through the capillary until a stable signal was obtained. The CHO cell membranes were injected and the baseline for the buffer is observed to change, demonstrating binding to the capillary.

The homogeneous samples are then flown through the capillary. The assay samples are run initially and then the capillary is washed with running buffer. The control samples are then run.

The control results are subtracted from the assay. The endpoint measurements are taken and plotted versus concentration. A one site binding (hyperbola) is fit to the curve (Y=Bmax*X/Kd+X) in order to determine the Kd.

4.4.3 Results

Figure 11:
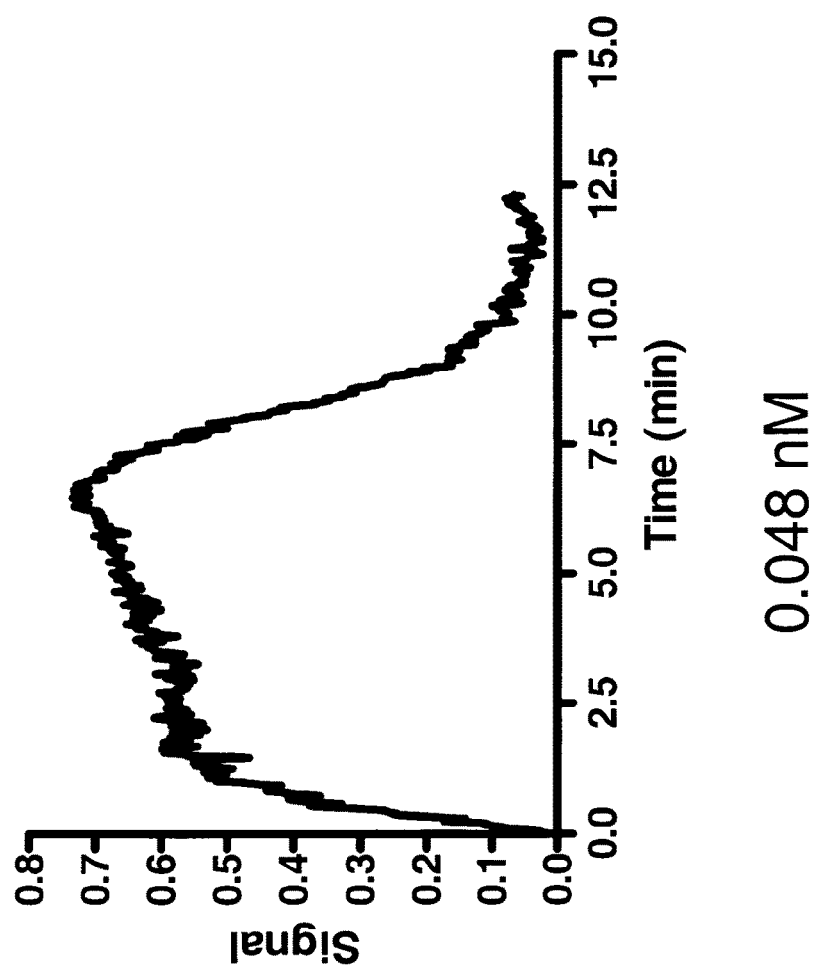
FIG. 11 shows an example data set of Experiment 2.
Figure 12:
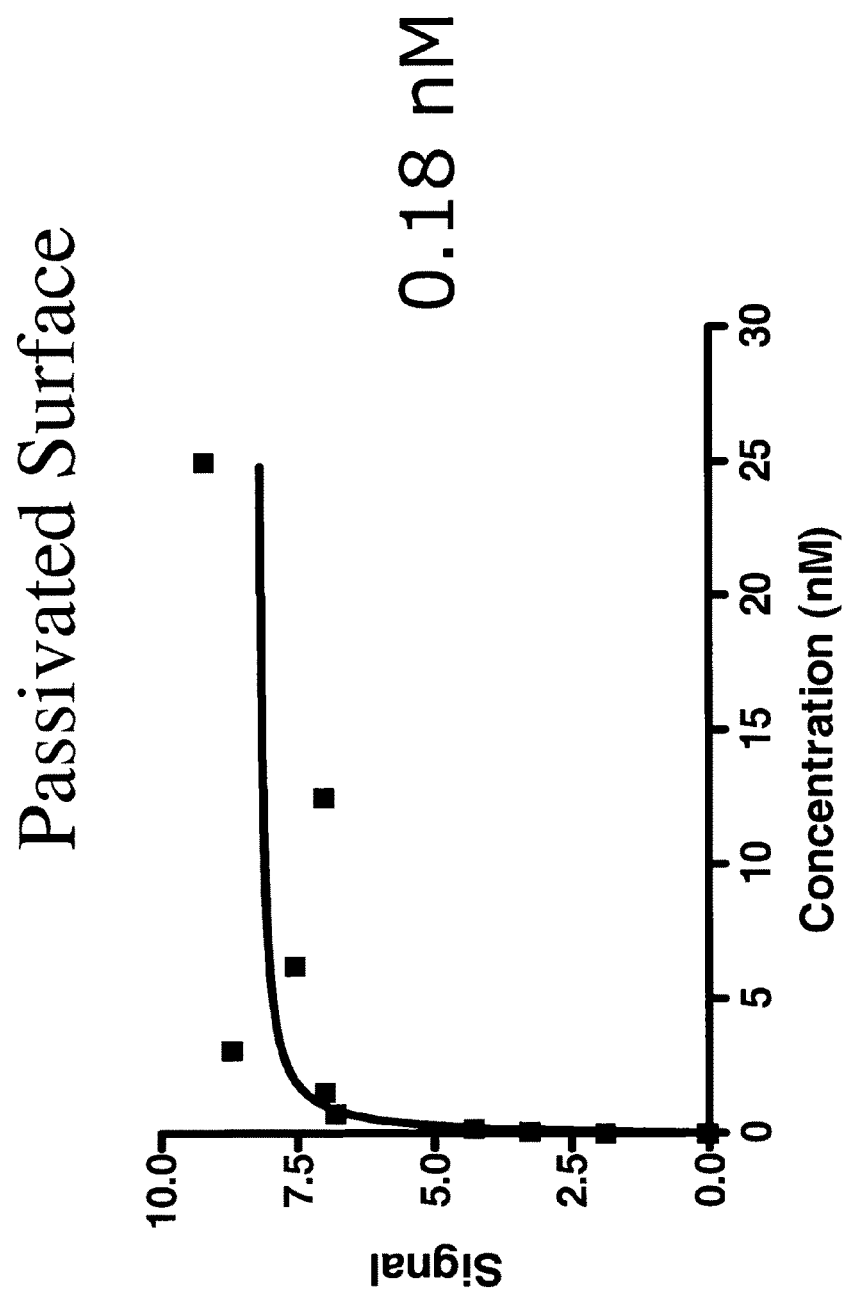
FIG. 12 shows combined data results for Experiment 2, a homogeneous assay with passivated surface.

FIG. 11 show that an example of the sample producing a change from the baseline for the control subtracted from the assay. The assay signal is a combined signal of the binding and the bulk RI change. The control signal is the bulk RI. The change from the baseline is then plotted versus concentration, FIG. 12. A one site binding (hyperbola) is fit to the curve (Y=Bmax*X/Kd+X) in order to determine the Kd. The Kd was calculated as 0.18 nM.

4.5 Experiment 3

Homogeneous Assay Employing Laminar Flow 4.5.1 Surface Chemistry
A bare capillary is used.
4.5.2 Performance of Assay
Sample is prepared as described in Experiment 2.

A bare capillary is inserted into the system. The running buffer is flown through the capillary until a stable signal is obtained. The homogeneous samples (both control and assay) are then injected into the system and the change from baseline is monitored. The signal obtained from the control samples is subtracted from the assay.

4.5.3 Results

Figure 13:
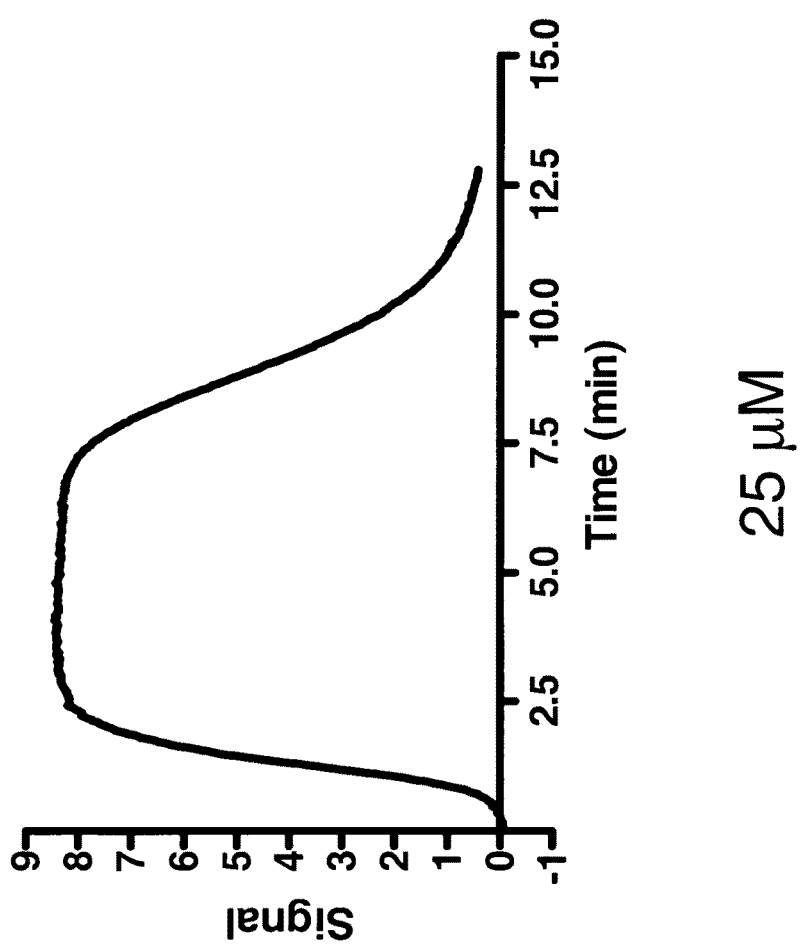
FIG. 13 shows an example data set of Experiment 3.
Figure 14:
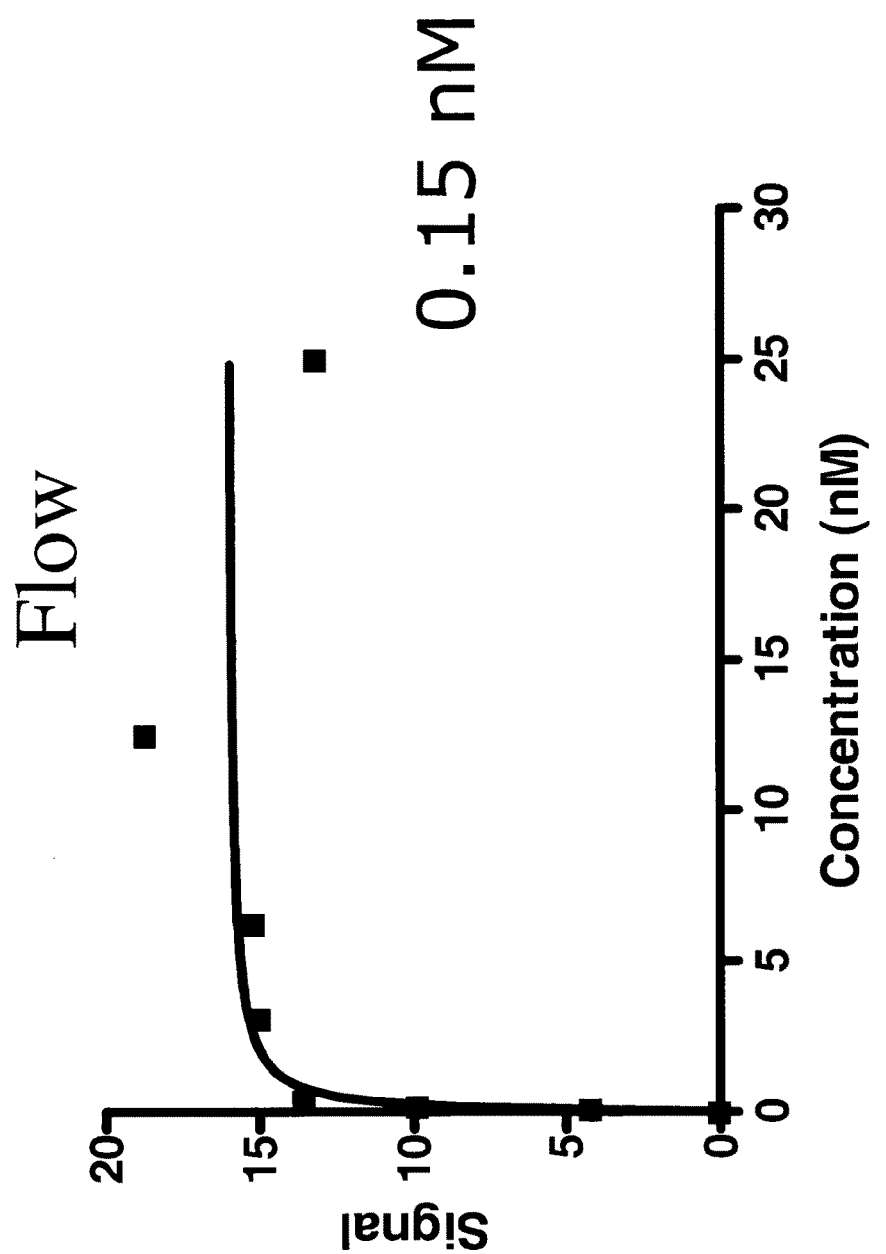
FIG. 14 shows combined data results for Experiment 3, a homogenous assay using bolus flow.

FIG. 13 shows an example of data over time where the control subtracted from the assay. FIG. 14 shows the concentrations of the Lys-(Des-Arg9)-Bradykinin and membranes were the same as in prior homogeneous assay. The analysis of the data is the same. The flow provides additional signal stability over a stop flow measurement. A Kd value of 0.15 nM was obtained.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for detecting a binding interaction between a membrane protein component and an analyte in a homogenous assay comprising:
    (I) providing a back scattering interferometer comprising:
        (a) a coherent light source;
        (b) a fluidic device comprising a fluidic channel comprising a wall surface, wherein the channel is configured to produce back-scattered light when interrogated by coherent light from the coherent light source, and wherein the wall surface has a passivating lipid membrane bound thereto through a membrane binding moiety that modifies the wall surface; and
        (c) a detector to detect the back-scattered light;
    (II) introducing into the fluidic channel a test lipid membrane having a membrane protein component disposed therein;
    (III) introducing into the fluidic channel an analyte;
    wherein the test lipid membrane and the analyte are introduced into the fluidic channel in free solution in a laminar flow environment, the passivating lipid membrane does not comprise the membrane protein component, and the test lipid membrane is introduced under conditions not to bind the passivating lipid membrane, and
    (IV) detecting a binding interaction between the membrane protein component and the analyte by back scattering interferometry.

2. The method of claim 1 wherein the concentration of the membrane protein component membrane protein in the fluidic sample is less than 1 micromolar.

3. The method of claim 1 which is performed label-free.

4. The method of claim 1 further comprising using a computer program to convert the detected back-scattered light into a parameter related to refractive index.

5. The method of claim 1 wherein the wall surface of the fluidic channel is modified by a method comprising: (i) reacting a mercapto-alkyloxysilane with wall surface hydroxyl groups to bind the silane to the wall surface; (ii) reacting the mercapto group with a maleimide succinic ester to generate a thioester moiety; (iii) reacting the thioester moiety with a molecule comprising an amine and a membrane binding moiety to generate a carbamate (thiocarbamate) bond to produce a membrane binding moiety and (iv) attaching a passivating membrane to the membrane binding moiety.

6. The method of claim 5 wherein the membrane binding moiety does not comprise a hydrophilic domain.

7. The method of claim 1 wherein the test lipid membrane and the analyte are introduced into the fluidic channel together.

8. The method of claim 1 comprising endpoint analysis or analysis performed in real time.

9. The method of claim 1 wherein the concentration of the component membrane protein in the fluidic sample is less than 1 nanomolar.

10. The method of claim 1 wherein the concentration of the component membrane protein in the fluidic sample is less than 100 picomolar.

11. The method of claim 1 wherein the test lipid membrane is in the form of a vesicle, a liposome, a monolayer lipid membrane, a bilayer-lipid membrane or a membrane incorporated with a receptor.

12. The method of claim 1 wherein the analyte comprises a drug candidate.

13. The method of claim 1 wherein the protein comprises a G protein-coupled receptor, an ion-channel receptor, a tyrosine kinase-linked receptor or a cytokine receptor.

14. The method of claim 1 wherein the membrane binding moiety comprises a hydrophobic or amphiphilic portion comprising a straight or branched chain alkyl, alkynyl, alkenyl, aryl, araalkyl, heteroalkyl, heteroalkynyl, heteroalkenyl, heteroaryl, or heteroaraalkyl group.

15. The method of claim 1 wherein the membrane binding moiety comprises a polyaliphatic chain.

16. The method of claim 1 wherein the fluidic channel is set up for detection under a stop flow configuration.

17. The method of claim 1 wherein the fluidic channel is set up for detection under a flowing configuration.

* * * * *